United States Patent [19]
Corbier et al.

[11] Patent Number: 5,650,414
[45] Date of Patent: *Jul. 22, 1997

[54] METHOD OF INHIBITING ANGIOTENSIN EFFECTS

[75] Inventors: Alain Corbier, Verrieres Le Buisson; Michel Fortin, Paris; Jacques Guillaume, Livry Gargan; Jean-Luc Haesslein, Courtry; Jean-Paul Vevert, Pantin, all of France

[73] Assignee: Roussel Uclaf, France

[*] Notice: The term of this patent shall not extend beyond the expiration date of Pat. No. 5,420,138.

[21] Appl. No.: 399,723

[22] Filed: Mar. 7, 1995

Related U.S. Application Data

[62] Division of Ser. No. 11,395, Jan. 29, 1993, Pat. No. 5,420,138.

[30] Foreign Application Priority Data

Jan. 31, 1992 [FR] France .................. 92 01084

[51] Int. Cl.$^6$ .................. A61K 31/435
[52] U.S. Cl. .................. 514/300
[58] Field of Search .................. 514/300

[56] References Cited

U.S. PATENT DOCUMENTS 5,420,138  5/1995  Corbier et al. .................. 514/300

FOREIGN PATENT DOCUMENTS 59-175491  10/1984  Japan .................. 546/121

OTHER PUBLICATIONS

Awano et al., Chem. Pharm. Bull., 34(7) pp. 2833–2839 (1986).

*Primary Examiner*—Bernard Dentz
*Attorney, Agent, or Firm*—Bierman, Muserlian and Lucas LLP

[57] ABSTRACT

The bicyclic derivatives of pyridines of the formula

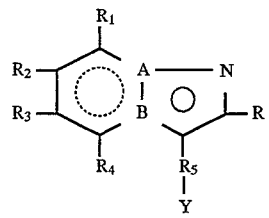

and their non-toxic, pharmaceutically acceptable salts and a process and intermediates for their preparation which compounds are inhibitors of angiotensin II effects, particularly a vasoconstrictor activity.

1 Claim, No Drawings

METHOD OF INHIBITING ANGIOTENSIN EFFECTS

PRIOR APPLICATION

This application is a division of U.S. patent application Ser. No. 011,395 filed Jan. 29, 1993, now U.S. Pat. No. 5,420,138.

It is of the invention to provide the novel compounds of formula I and their non-toxic, pharmaceutically acceptable salts with acids and bases and a novel process and intermediates for their preparation.

OBJECTS OF THE INVENTION

It is an object of the invention to provide novel vasoconstrictive compositions and a novel method of inducing vasoconstrictive activity in warm-blooded animals.

These and other objects and advantages of the invention will become obvious from the following detailed description.

THE INVENTION

The novel compounds of the invention are compounds selected from the group consisting of all possible racemic isomers, enantiomers and diastereoisomers of a compound of the formula

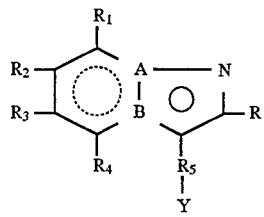 I wherein one of A and B is nitrogen and the other is carbon, the dotted lines indicate that the pyridinyl ring is optionally unsaturated, R is selected from the group consisting of optionally cycloalkyl of 3 to 7 carbon atoms and cycloalkyl alkyl of 4 to 10 carbon atoms, $R_1$, $R_2$, $R_3$ and $R_4$ are individually selected from the group consisting of a) $-(CH_2)_{m1}-S(O)_{m2}-X-R_{14}$, m1 is an integer from 0 to 4, m2 is an integer from 0 to 2, when m1 is other than 0, $X-R_{14}$ is $-NH_2$ or mono or di-alkyl or alkenyl-amino of up to 6 carbon atoms or mono or di-phenyl amino all optionally substituted with at least one member of the group consisting of halogen, —OH, alkyl and alkoxy of 1 to 4 carbon atoms, $-CF_3$, free, esterified or salified carboxy, —CN and tetrazolyl and whatever the value of m1, $R_{14}$ is selected from the group consisting of optionally substituted alkyl and alkenyl of up to 6 carbon atoms and optionally substituted aryl with at least one member of the group consisting of —OH, halogen, alkyl and alkoxy of 1 to 4 carbon atoms, $-CF_3$, free, esterified, salified or amidified carboxy, —CN and tetrazolyl and X is selected from the group consisting of a single bond,

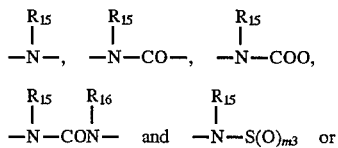

-continued

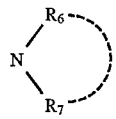

m3 is an integer from 0 to 2, $R_{15}$ and $R_{16}$ are individually hydrogen or $R_{14}$ and is defined as in e), b) hydrogen, halogen, —OH, —CN, —NO$_2$, sulfonyl, formyl, benzoyl, acyl of up to 12 carbon atoms and free, salified esterified or amidified carboxy, c) alkyl, alkenyl, alkynyl, alkoxy, acyloxy, alkythio, alkylsulfinyl or alkylsulfonyl all having up to 6 carbon atoms and optionally substituted, d) cycloalkyl, aryl, arylalkyl, arylalkenyl, aryloxy, aralkoxy, arylthio, arylsulfinyl and arylsulfonyl, the alkyl and alkenyl portion having up to 6 carbon atoms and the aryl is a monocylic of 5 to 6 ring members or a condensed ring of 8 to 14 ring members optionally containing at least one heteroatom selected from the group consisting of oxygen, sulfur and nitrogen and optionally substituted, e)

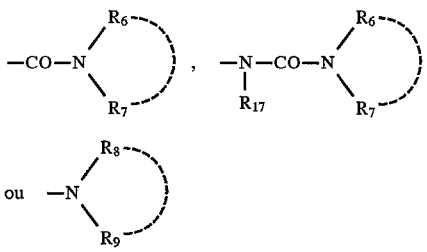

$R_{17}$, $R_6$, $R_7$, $R_8$ and $R_9$ are individually selected from the group consisting of hydrogen, alkyl and alkenyl of up to 6 carbon atoms optionally substituted with a member of the group consisting of halogen, —OH and alkoxy of 1 to 6 carbon atoms, $-(CH_2)_{m1}-S(O)_{m2}-X-R_{14}$ and aryl and arylalkyl of 1 to 6 alkyl carbon atoms and the aryl is monocyclic of 5 to 6 ring members or a condensed cycle of 8 to 14 ring members optionally containing at least one heteroatom selected from the group consisting of oxygen, sulfur and nitrogen and optionally substituted with at least one member of the group consisting of halogen, —OH, —NO$_2$, free, salified, esterified or amidified carboxy and alkyl, alkenyl, alkoxy and acyl of up to 6 carbon atoms or $R_6$ and $R_7$ or $R_8$ and $R_9$ taken with the nitrogen atom form a monocyclic of 5 to 6 ring members or a condensed cyclic of 8 to 14 ring members optionally containing at least one heteroatom selected from the group consisting of —O—, —S— and nitrogen and optionally substituted with at least one member of the group consisting of halogen, —OH, —NO$_2$, free, salified, esterified or amidified carboxy and alkyl, alkenyl, alkoxy and acyl of up to 6 carbon atoms or $R_8$ and $R_9$ are individually acyl of a carboxylic acid of up to 6 carbon atoms, $R_5$ is selected from the group consisting of alkylene of 1 to 4 carbon atoms or

Y is —Y$^1$—B—Y$_2$, Y$_1$ is a monocyclic arylene of 5 to 6 ring members or condensed rings of 8 to 14 ring members optionally containing at least one member of the group consisting of —O—, —S— and nitrogen and optionally substituted with at least one of the substituents of R$_1$, R$_2$, R$_3$ and R$_4$ and B is a single bond between Y$_1$ and Y$_2$ or is a divalent member of the group consisting of —CO—, —NH—CO—, —CO—NH— and —O—(CH$_2$)$_n$— and n is 0, 1, 2 or 3, and if B is a simple bond, Y$_2$ is selected from the group consisting of hydrogen, —CN, free, salified, esterified or amidified carboxy, tetrazolyl and —(CH$_2$)$_{m1}$—S(O)$_{m2}$—X—R$_{14}$ as defined above or when B and Y$_2$ are the same or different from Y, the values defined for Y$_1$ and their non-toxic, pharmaceutically acceptable salts with bases and acids.

Examples of the bicycles formed by

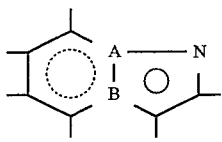

where A, B and the dotted line have the above definition include the following

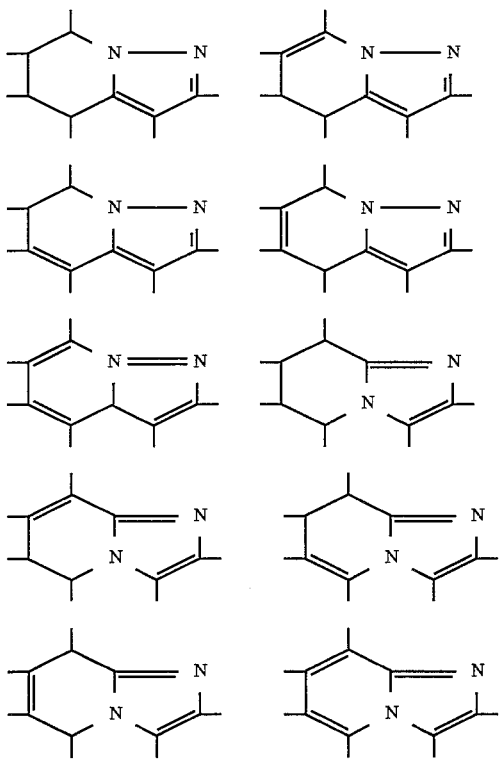

Examples of alkyl are methyl, ethyl, n-propyl, isopropyl, n-butyl, sec-butyl, isobutyl, tert-butyl, pentyl, hexyl, isopentyl and isohexyl and examples of alkoxy are methoxy, ethoxy, propoxy, isopropoxy, n-butoxy, sec-butoxy and tert-butoxy. Examples of alkenyl are vinyl, allyl, 1-propenyl, 1-butenyl and pentenyl and examples of alkynyl are ethynyl, propargyl, butynyl and pentynyl.

Examples of halogen are fluorine, bromine, iodine but preferably chlorine. Examples of acyl of a carboxylic acid are formyl, acetyl, propionyl, butyryl, benzoyl, pentanoyl, hexanoyl, acryloyl, crotonoyl and carbamoyl. Examples of amino substituted by one or two alkyl or alkenyl are methylamino, ethylamino, dimethylamino and ethylmethylamino.

The acyloxy may be derived from the acyls discussed above and are preferably formyloxy, acetyloxy, propionyloxy, butyryloxy and benzoyloxy. Examples of cycloalkyl are cyclopropyl, cyclobutyl, cyclopentyl and cyclohexyl.

Examples of saturated monocycles of 5 to 7 ring members are cyclopentyl and cyclohexyl and examples of unsaturated monocycles are cyclopentenyl, cyclohexenyl, cyclopentadienyl, cyclohexadienyl. Examples of aromatic carbocycles are phenyl. Examples of saturated monocyclic heteroaryls are pyrrolidinyl, imidazolidinyl, pyrazolidinyl, piperidyl, piperazinyl, morpholinyl, thiomorpholinyl and azepinyl and examples of unsaturated monocyclic heterocyclics are thienyl, furyl, pyrannyl, pyrrolyl, imidazolyl, pyrazolyl, pyridyl, pyrazinyl, pyrimidinyl, pyridazinyl, thiazolyl, thiadiazolyl, oxazolyl, furazannyl, pyrrolinyl such as 2-pyrrolinyl, imidazolinyl such as Δ 2-imidazolinyl, pyrazolinyl such as Δ 3-pyrazolinyl and isomers of one or more of the heteroatoms such as isothiazolyl and isooxazolyl.

Examples of saturated condensed carboxylic rings are indanyl bicyclo [4,4,0] decyl and indanyl bicyclo [4,4,1] undecyl and examples of unsaturated condensed carbocyclics are naphthyl, phenanthryl and indenyl. Examples of saturated condensed heterocyclics are 1-oxa-spiro [4,5] decyl, tetrahydropyrann-2-spirocyclohexyl, cyclohexanespiro-2'-(tetrahydrofuran) or 1,10-diazaanthr-4-yl and examples of unsaturated condensed heterocyclics are benzothienyl, naphtho [2,3-b] thienyl, indenyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phtalazinyl, naphthypiridinyl, quinoxalinyl, quinazolinyl, cinnolinyl, pteridinyl, carbazolyl, beta carbolinyl, acridinyl, phenazinyl, phenothiazinyl, phenoxazinyl, indolinyl and isoindolinyl. Examples of polycyclic condensed systems having monocyclic heterocyclics are furo [2,3-b] pyrrol or thieno [2,3-b] furan.

The term "aryl" includes unsaturated monocyclic or condensed carbocyclic and heterocyclic ring systems optionally containing at least one —O—, —S— or nitrogen. Examples of aryl are phenyl, naphthyl, thienyl such as 2-thienyl and 3-thienyl, furyl such as 2-furyl, pyridyl such as 3-pyridyl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl. Examples of condensed heterocyclics containing at least one of —O—, —S— and nitrogen are 3-benzothienyl, benzofuryl, benzopyrrolyl, benzimidazolyl, benzoxazolyl, thionaphthyl, indolyl and purinyl.

In the aralkyl and aralkenyl, the aryl is defined as above and examples include benzyl, diphenylmethyl, triphenylmethyl, naphthylmethyl, indenylmethyl, thienylmethyl such as 2-thienylmethyl, furylmethyl such as furfuryl, pyridylmethyl, pyrimidyl or pyrrolylmethyl. The alkyl can also be other alkyls such as ethyl, propyl or butyl like phenethyl. Examples of arylalkenyl are phenylvinyl, phenylallyl, pyridylvinyl, naphthylvinyl and naphthylallyl. The list is not intended to be exhaustive.

Examples of haloalkyl are the above alkyls substituted with at least one halogen such as bromoethyl, trifluoromethyl, trifluoroethyl and pentafluoroethyl.

Examples of alkylthio are the above alkyls such as methylthio, ethylthio and examples of halogenated alkoxy and halogenated alkylthio are bromoethylthio, trifluoromethylthio, trifluoroethylthio, pentafluoroethylthio, bromoethoxy, trifluoromethoxy, trifluoroethoxy and pentafluoroethoxy.

Examples of aryloxy and arylalkoxy with aryl as defined above are phenoxy, benzyloxy, phenethoxy and phenylisopropoxy. The carbamoyl may be mono lower alkyl and di lower alkyl substituted such N-methyl carbamoyl, N-ethyl-carbamoyl, N,N-dimethyl-carbamoyl and N,N-diethyl-carbamoyl or substituted with hydroxy alkyl such as N-(hydroxymethyl)-carbamoyl and N-(hydroxyethyl)-carbamoyl. The carbamoyl may also be carbamoylalkyl such as carbamoylmethyl or carbamoylethyl.

Acyloxy may be derived from the acyls discussed above and examples are acetoxy and propionyloxy. The arylthio and aralkylthio have the aryl defined as above and examples include phenylthio and benzylthio.

$R_1$, $R_2$, $R_3$ and $R_4$ may be also alkylthio, arylthio, alkylsulfinyl, alkylsulfonyl, arylsulfinyl, arylsulfonyl and cycloalkylthio such as cyclohexylthio. The alkylthio, alkylsulfinyl and alkylsulfonyl have the alkyls as discussed above and may be substituted as discussed above. Examples of such group are methylthio, ethylthio, hydroxyethylthio, aminoethylthio, methylsulfinyl, ethylsulfinyl, methylsulfonyl, propylthio, butylthio, sec-butylthio, tert-butylthio, isopentylthio and isohexylthio as well as the oxidized sulfinyl and sulfonyl derivatives.

The arylthio, arylsulfinyl and arylsulfonyl have the aryl as defined above and examples include phenylthio, pyridylthio, pyrimidylthio, imidazolylthio and N-methylimidazolylthio and the corresponding compounds where the thio is oxidized to sulfinyl or sulfonyl such as phenylsulfinyl and phenylsulfonyl.

The aralkyls and aralkenyls have the aryl and alkyl as defined above and examples of aralkyl are benzyl, diphenylmethyl, triphenylmethyl, naphthylmethyl, indenylmethyl, thienylmethyl such as 2-thienylmethyl, furylmethyl such as furfuryl, pyridylmethyl, pyrimidylmethyl and pyrrolylmethyl and higher alkyl such as phenethyl. Examples of aralkenyl are phenylvinyl, phenylallyl, naphthylvinyl, naphthylallyl, pyridylallyl.

The carbocyclic and heterocyclic groups are defined as above and include phenyl, benzyl, phenethyl, naphthyl, indolyl, indolinyl, thienyl, furyl, pyrrolyl, pyridyl, pyrrolidinyl, piperidino, morpholino and piperazinyl and optionally substituted such as methylpiperazinyl, fluoromethylpiperazinyl, ethylpiperazinyl, propylpiperazinyl, phenylpiperazinyl and benzylpiperazinyl.

The carbamoyl, amino and ureido may be optionally substituted as discussed above and may have the formulae

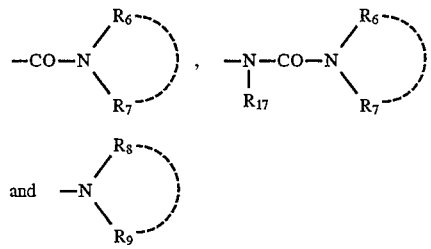

wherein $R_6$, $R_7$, $R_8$ and $R_9$ are individually selected from the group consisting of hydrogen, alkyl and alkoxyalkyl such as methyl, ethyl, isopropyl, methoxymethyl, methoxyethyl and ethoxyethyl; carbocyclic and heterocyclic such as phenyl, benzyl, phenethyl, naphthyl, indolyl, indolinyl, thienyl, furyl, pyrrolyl, pyridyl, pyrrolidinyl, piperidino, morpholino and piperazinyl and optionally substituted such as methylpiperazinyl, fluoromethylpiperazinyl, ethylpiperazinyl, propylpiperazinyl, phenylpiperazinyl and benzylpiperazinyl.

Examples of amino acids are those derived from natural amino acids such as glycine, alanine, valine and other known amino acids.

$R_6$ and $R_7$ or $R_8$ and $R_9$ together with the nitrogen to which they are attached may form an heterocycle such as pyrrolyl, imidazolyl, pyrazinyl, indolyl, indolinyl, purinyl, pyrrolidinyl, piperidyl, piperidino, morpholino, piperazinyl, imidazolidinyl, pyrazolidinyl, thiomorpholinyl and azepine and may be optionally substituted by at least one member of the group consisting of chlorine, fluorine, methyl, ethyl, isopropyl, tert-butyl, methoxy, ethoxy, propoxy, benzoyl, methoxycarbonyl and ethoxycarbonyl. Examples are methylpiperazinyl, ethylpiperazinyl, propylpiperazinyl, phenylpiperazinyl and benzylpiperazinyl. In the last groups, phenyl and benzyl are preferably substituted as discussed above for aryl, aralkyl and aralkenyl such as chlorophenyl or trifluorophenyl. The said formed heterocyclics are preferably saturated. In addition, $R_8$ and $R_9$ may be acyl as discussed above such as acetyl, propionyl, butyryl, pentanoyl and carbamoyl.

$R_1$, $R_2$, $R_3$ and $R_4$ may also be carbamoyl or amino of the formulae

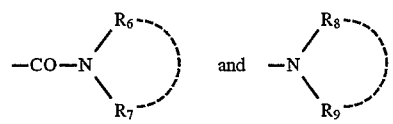

wherein $R_6$ and $R_7$ are individually aliphatic or cyclic chains or $R_6$ and $R_7$ or $R_8$ and $R_9$ together with the nitrogen to which they are attached from a heterocyclic as defined above. The carbamoyl

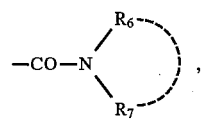

the ureido

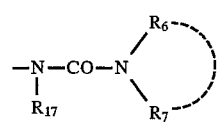

and amino

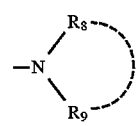

may be substituted with 1 or 2 of the groups discussed above. Examples of the substituted carbamoyl are N-mono lower alkyl carbamoyl such as N-methyl carbamoyl, N-ethyl carbamoyl; N-di lower alkyl carbamoyl such as N,N-dimethyl-carbamoyl and N,N-diethyl-carbamoyl; N-(hydroxy lower alkyl) carbamoyl such as N-(hydroxymethyl)- carbamoyl and N-(hydroxyethyl)-carbamoyl; carbamoyl lower alkyl such as carbamoylmethyl and carbamoylethyl; phenylcarbamoyl; pyridylcarbamoyl; benzylcarbamoyl; N-methyl N-phenylcarbamoyl; pyridylmethylcarbamoyl. The amino may be substituted with 1 or 2 lower alkyls such as methyl, ethyl or isopropyl. When $R_8$ or $R_9$ is alkoxycarbamoyl, it is preferably tert-butoxycarbamoyl or benzyloxy carbamoyl.

The ureido group is preferably —NH—CO—NH—aryl, —NH—CO—NH—alkyl, N(alkyl)—CO—N(alkyl)$_2$ and particularly —NH—CO—NH—tetrazolyl and —N(alkyl)—CO—NH—tetrazolyl, wherein the alkyl and aryl is defined as above.

$R_5$ in the compounds of formula I is —CO— or preferably methylene or ethylene.

$Y_1$ and $Y_2$ have the values reported above for monocyclic aryl or condensed rings and in the case of B being a single bond, $Y_2$ can also be hydrogen, —CN, —(CH$_2$)$_{m1}$—SO$_{m2}$—X—$R_{14}$ or free, salified, esterified or amidified carboxy.

$Y_1$ and $Y_2$ are individually aryl optionally substituted with at least one member of the group consisting of halogen, —OH, —NO$_2$, tetrazolyl, free, salified or esterified carboxy, alkyl, alkenyl, alkoxy, acyl and —(CH$_2$)$_m$—SO$_{m2}$—X—$R_{14}$.

Among preferred compounds of formula I are those in which $Y_1$ is not substituted and $Y_2$ is substituted by free or esterified carboxy, tetrazolyl or —(CH$_2$)$_{m1}$—S(O)$_{m2}$—X—$R_{14}$.

The carboxyls of formula I may be salified, esterified or amidified by groups well known to those skilled in the art. The salification may be effected with sodium, potassium, lithium, ammonia and equivalents of calcium or magnesium or organic bases such as methylamine, propylamine, trimethylamine, diethylamine, triethylamine, N,N-dimethylethanolamine, pyridine, picoline, dicyclohexylamine, morpholine, benzylamine, procaine, lysine, arginine, histidine and N-methyl-glucamine.

Among the esterification compounds, alkyl to form alkoxycarbonyl are methoxycarbonyl, ethoxycarbonyl, tert-butoxycarbonyl or benzyloxycarbonyl and the alkyls may be substituted by a member selected from the group consisting of halogen, hydroxyl, alkoxy, acyl, acyloxy, alkylthio, amino and aryl. Examples are chloromethyl, hydroxypropyl, methoxymethyl, propionyloxymethyl, methylthiomethyl, dimethylaminoethyl, benzyl and phenethyl.

Among the amidification compounds are —CO$_2$—NH—COOH, —CO$_2$—NH—COOaryl, —CO$_2$—NH—COOalkyl, —CO$_2$—NH—SO$_2$—Oalkyl, —CO$_2$—NH—SO$_2$—Oaryl and —CO$_2$—NH—SO$_2$—N(alkyl)$_2$, in which the alkyl and aryl have the meanings indicated above and are optionally substituted as also indicated above. Particularly preferred as aryl are optionally salified phenyl and tetrazolyl. Amidified carboxy includes:

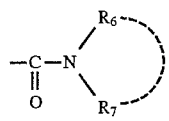

in which $R_6$ and $R_7$ have the previous meaning.

The addition acid salts with mineral or organic acids of the products of formula I can be formed with the following acids: hydrochloric, hydrobromic, hydroiodic, nitric, sulfuric, phosphoric, propionic, acetic, formic, benzoic, maleic, fumaric, succinnic, tartaric, citric, oxalic, glyoxylic, aspartic, ascorbic acids, alkylmonosulfonic acids such as methanesulfonic, ethanesulfonic, propanesulfonic, alkyldisulfonic acids such as methanedisulfonic acids, alpha, beta-ethanedisulfonic, arylmonosulfonic such as benzenesulfonic and aryldisulfonic acids.

$R_1$, $R_2$, $R_3$ and $R_4$ can also be alkyl, aryl, free, salified, esterified or amidified carboxy, alkylthio, alkenylthio or alkynylthio optionally substituted by at least one member selected from the group consisting of formyl; hydroxyl; alkoxy; acyloxy; free, salified or esterified carboxy; amino; substituted amino; carbamoyl; substituted carbamoyl; mercapto; alkylthio; acylthio such as acetylthio; arylthio such as phenylthio; sulfo, cycloalkyl such as cyclohexyl; pyridinyl; pyrimidinyl; phenyl.

The amino and carbamoyl can be substituted by one or two alkyls and amino acids chosen from the 20 natural amino acids such as proline, glycine, alanine, leucine, isoleucine, valine or phenylalanine.

The alkylthio substituted by one or more halogens such as chlorine and fluorine, can be

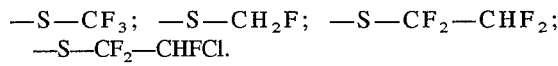
—S—CF$_2$—CHFCl.

$R_1$, $R_2$, $R_3$ and $R_4$ that can be carried by the ring

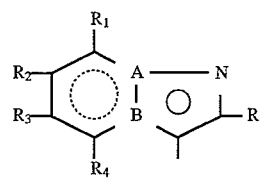

or that can be carried by Y as defined above, can be wherein m, m1 and m2 are individually an integer from 0 to 6,

—S—CH$_3$;

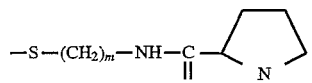

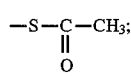

—SO$_3$H
—S—(CH$_2$)$_{m1}$—S—(CH$_2$)$_{m2}$—X$_1$;
—S—(CH$_2$)$_m$—X$_1$;
—S—(CH$_2$)$_{m1}$—NH—(CH$_2$)$_{m2}$—X$_1$;
—S—CH=CH—(CH$_2$)$_m$—X$_1$;
—S—(CH$_2$)$_{m1}$—CH=CH—(CH$_2$)$_{m2}$—X$_1$;
—S—C≡C—(CH$_2$)$_m$—X$_1$;

in which X$_1$ is H, OH, cyclohexyl, pyridyl, pyrimidyl, phenyl, naphthyl, CHO, COOH, NH$_2$ or

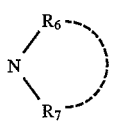

$R_1$, $R_2$, $R_3$ and $R_4$ can also preferably be

—COOH; —NH$_2$;—C≡N; —OCH$_3$; —OCH$_2$—CH$_3$; —CH=CH—COOH; tetrazolyl;

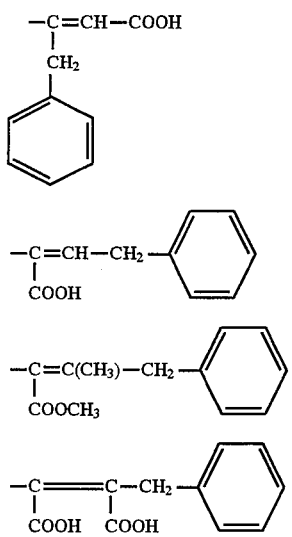

in all their isomer, cis-trans isomer forms.

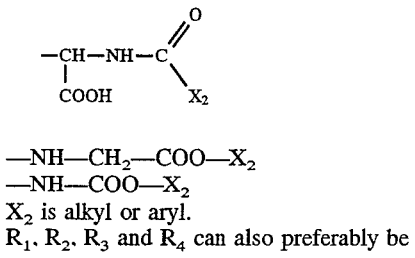

—NH—CH₂—COO—X₂
—NH—COO—X₂
X₂ is alkyl or aryl.
R₁, R₂, R₃ and R₄ can also preferably be

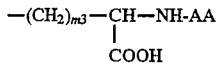

in which m3 is an integer for 0 to 4 and AA is a natural amino acid such as proline or glycine and

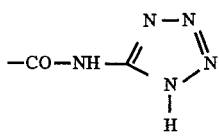

The preferred products of formula I are those wherein R₁, R₂, R₃ and R₄ are hydrogen, optionally substituted alkyl, alkylthio, alkoxy as defined above, or free, salified or esterified, or amidified carboxy such as —COOH, —COO methyl, —CONH₂ or

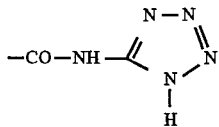

To these meanings indicated above for R₁, R₂, R₃ and R₄ in the products of formula I are added the values indicated above for Y which can represent particularly biphenyl radical, Y being substituted and preferably in ortho position of the second ring when Y is biphenyl, by one or more members chosen from formyl, free salified, esterified or amidified carboxy, cyano, tetrazolyl and amino, optionally substituted and —(CH₂)$_{m1}$—SO₂—X—R₁₄, as defined above and preferably:

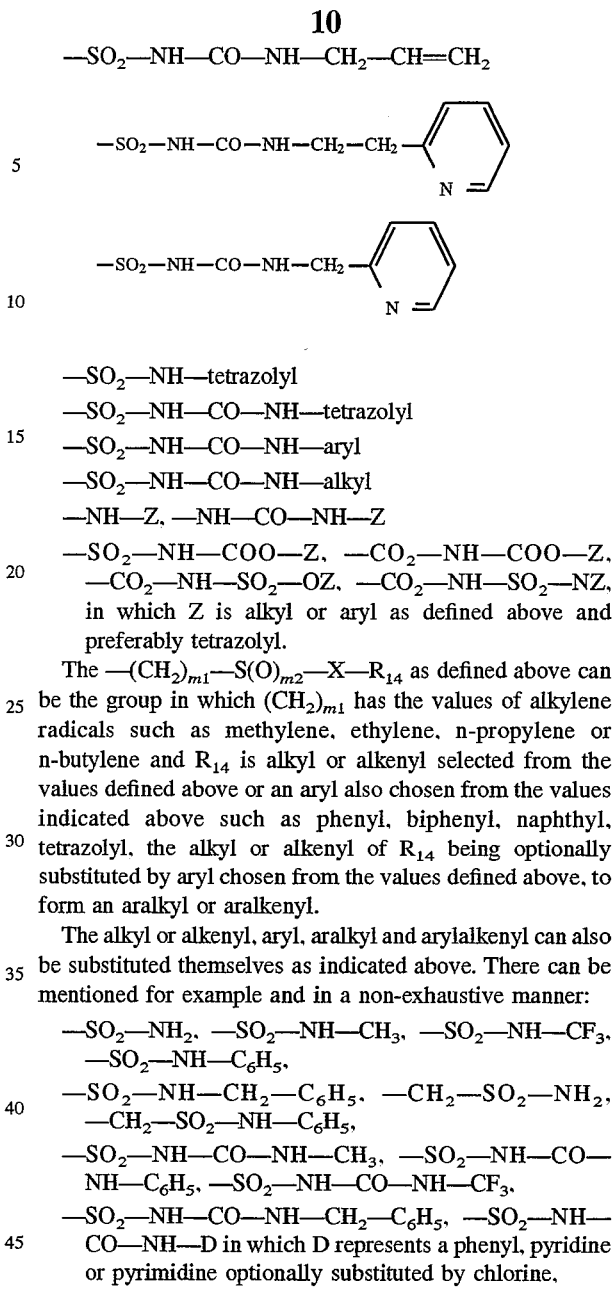

—SO₂—NH—tetrazolyl
—SO₂—NH—CO—NH—tetrazolyl
—SO₂—NH—CO—NH—aryl
—SO₂—NH—CO—NH—alkyl
—NH—Z, —NH—CO—NH—Z
—SO₂—NH—COO—Z, —CO₂—NH—COO—Z, —CO₂—NH—SO₂—OZ, —CO₂—NH—SO₂—NZ,
in which Z is alkyl or aryl as defined above and preferably tetrazolyl.

The —(CH₂)$_{m1}$—S(O)$_{m2}$—X—R₁₄ as defined above can be the group in which (CH₂)$_{m1}$ has the values of alkylene radicals such as methylene, ethylene, n-propylene or n-butylene and R₁₄ is alkyl or alkenyl selected from the values defined above or an aryl also chosen from the values indicated above such as phenyl, biphenyl, naphthyl, tetrazolyl, the alkyl or alkenyl of R₁₄ being optionally substituted by aryl chosen from the values defined above, to form an aralkyl or aralkenyl.

The alkyl or alkenyl, aryl, aralkyl and arylalkenyl can also be substituted themselves as indicated above. There can be mentioned for example and in a non-exhaustive manner:

—SO₂—NH₂, —SO₂—NH—CH₃, —SO₂—NH—CF₃, —SO₂—NH—C₆H₅,
—SO₂—NH—CH₂—C₆H₅, —CH₂—SO₂—NH₂, —CH₂—SO₂—NH—C₆H₅,
—SO₂—NH—CO—NH—CH₃, —SO₂—NH—CO—NH—C₆H₅, —SO₂—NH—CO—NH—CF₃,
—SO₂—NH—CO—NH—CH₂—C₆H₅, —SO₂—NH—CO—NH—D in which D represents a phenyl, pyridine or pyrimidine optionally substituted by chlorine,

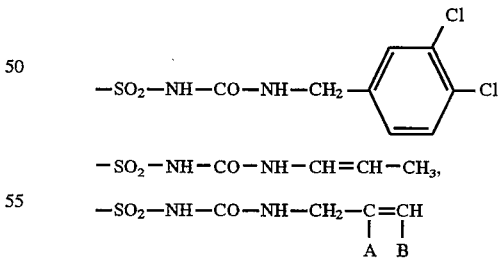

in which A and B are chosen from the hydrogen, phenyl, pyridyl and pyrimidyl,

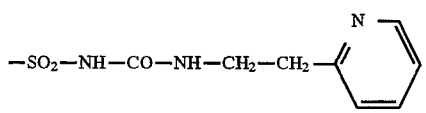

-continued

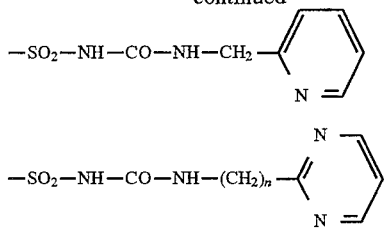

with n=1 or 2

The aryl of $Y_1$ can be substituted by at least one member chosen from the values of $R_2$ and $R_3$ and particularly by the —NH—$(CH_2)_m$—$SO_2$—X—$R_{14}$ and —CO—NH—$(CH_2)_m$—$SO_2$—X—$R_{14}$ in which $(CH_2)_m$—$SO_2$—X—$R_{14}$ can be for example the values indicated above.

The following can be mentioned in a non-exhaustive manner:

—NH—$SO_2$—$CH_3$, —NH—$SO_2$—$C_6H_5$, —NH—$SO_2$—$CF_3$, —NH—$CH_2$—$SO_2$—NH—$C_6H_5$, —CO—NH—$SO_2$—$C_2H_5$, —CO—NH—$SO_2$—$CH_3$, —CO—NH—$SO_2$—$CH_2$—$C_6H_5$.

Preferably the compounds of formula I can have as for:

a) alkyl, alkenyl, alkynyl, cycloalkyl and cycloalkyl alkyl of R.

b) alkyl, alkenyl, alkynyl, alkoxy, acyloxy, alkylthio, alkylsulfinyl and alkylsulfonyl of $R_1$, $R_2$, $R_3$ and $R_4$.

c) cycloalkyl, aryl, arylalkyl, arylalkenyl, aryloxy, arylalkoxy, arylthio, arylsulfinyl and arylsulfonyl of $R_1$, $R_2$, $R_3$ and $R_4$, are selected from the group consisting of:

halogen, hydroxyl, cyano, nitro, formyl, acyl of at most 6 carbon atoms, benzoyl, carboxy free, salified or esterified by an alkyl of at most 6 carbon atoms, alkyl and alkenyl of at most 6 carbon atoms and optionally substituted by at least one substituent chosen from halogen, hydroxyl and alkoxy of at most 6 carbon atoms, alkoxy of at most 6 carbon atoms, aryl and aralkyl with alkyl of at most 6 carbon atoms, these aryl and aralkyl being such that the aryl represents a monocyclic of 5 or 6 ring members or condensed rings of 8 to 14 ring members, optionally containing at least one heteroatom chosen from oxygen, nitrogen and sulfur atoms, and optionally substituted by at least one member chosen from halogen, hydroxyl, nitro, alkyl, alkenyl, alkoxy and acyl of at most 6 carbon atoms, free, salified, esterified or amidified carboxy,

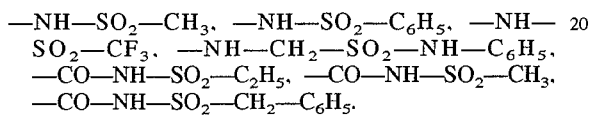

in which either $R_{10}$ and $R_{11}$ or $R_{12}$ and $R_{13}$ are individually hydrogen, an alkyl or alkenyl of at most 6 carbon atoms optionally substituted by at least one member chosen from halogen, hydroxyl and alkoxy of at most 6 carbon atoms, aryl or aralkyl with alkyl of at most 6 carbon atoms, the aryl being a monocyclic of 5 or 6 ring members or condensed rings of 8 to 14 ring members optionally containing at least one heteroatom chosen from oxygen, nitrogen and sulfur, and optionally substituted by at least one member chosen from halogen, hydroxyl, nitro, alkyl, alkenyl, alkoxy and acyl of at most 6 carbon atoms, free, salified, esterified or amidified carboxy, or $R_{10}$ and $R_{11}$ or $R_{12}$ and $R_{13}$ form with the nitrogen atom to which they are attached, a monocyclic of 5 or 6 ring members or condensed rings of 8 to 14 ring members optionally containing at least one heteroatom chosen from oxygen, nitrogen and sulfur and optionally substituted by at least one member chosen from halogen, hydroxyl, nitro, alkyl, alkenyl, alkoxy and acyl of at most 6 carbon atoms, free, salified, esterified or amidified carboxy, or $R_{12}$ and $R_{13}$ are individually an acyl of a carboxylic acid of at most 6 carbon atoms, the said products of formula I being in all possible racemic, enantiomeric and diastereoisomeric isomer forms, as well as the addition salts with mineral and organic acids or with mineral and organic bases thereof.

Preferably the compounds of formula I have the formula:

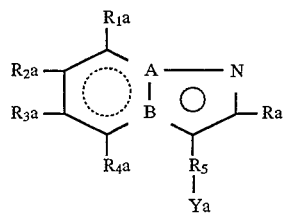

Ia in which one of A or B is a nitrogen and the other is a carbon atom, the heterobicycle thus formed being saturated or unsaturated, Ra is alkyl of at most 4 carbon atoms, $R_1a$, $R_2a$, $R_3a$ and $R_4a$ are individually chosen from the group formed by hydrogen, hydroxyl, alkoxy of at most 6 carbon atoms, alkyl of at most 6 carbon atoms and optionally substituted by at least one substituent chosen from halogen, hydroxyl, alkoxy of at most 4 carbon atoms, amino and carbamoyl, free carboxy, carboxy esterified by alkyl of at most 4 carbon atoms, $R_5$ is divalent alkylene of 1 to 4 carbon atoms, or —C═O, Ya is —$Y_1a$—Ba—$Y_2a$, $Y_1a$ is phenyl, —Ba is a single bond or —CO—NH—, $Y_2a$ is, either if Ba is a single bond or —CO—NH—, is a phenyl optionally substituted by at least one member chosen from halogen, free, salified or esterified carboxy, cyano, tetrazolyl, pyrazolo(1-5a)pyridine, [pyrazolo(1-5a)pyridin]alkyl, imidazo(1-2a)pyridine, [imidazo(1-2a)pyridin]alkyl and —$(CH_2)_p$—$SO_2$—Xa—$R_{14}a$ in which p is 0 or 1, Xa is a single bond or —NH—, —NH—CO— and NH—CO—NH—, and $R_{14}a$ is methyl, ethyl, propyl, vinyl, allyl, pyridyl, phenyl, benzyl, pyridylmethyl, pyridylethyl, pyrimidyl, tetrazolyl, thiazolyl, diazolyl, piperidinyl or tetrahydrofurannyl, all optionally substituted by at least one member chosen from halogen, hydroxyl, alkyl and alkoxy of at most 6 carbon atoms, trifluoromethyl, cyano and nitro, or if Ba is a single bond, $Y_2a$ may be halogen, cyano, free, salified or esterified carboxy or tetrazolyl.

Other preferred compounds of formula I are those of the formula

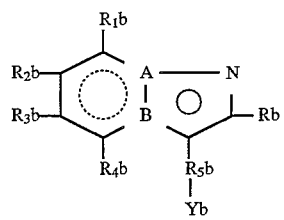

Ib in which one of A or B is nitrogen and the other is a carbon atom so that the heterobicycle is imidazo pyridine, pyrazolo pyridine or pyrazolo tetrahydropyridine imidazotetrahydropyridine, Rb is an n-butyl or methyl, $R_1b$, $R_2b$, $R_3b$ and $R_4b$ are such that three of them are hydrogen and the other is hydrogen, carboxy free or esterified by alkyl of at most 4 carbon atoms, $R_5b$ is methylene or —C=O and Yb is phenyl or biphenyl substituted by halogen, cyano, carboxy free or esterified by alkyl, tetrazolyl or [pyrazolo (1-5a)pyridin]alkyl in which the [pyrazolo(1-5a)pyridin] can be substituted by one or two alkyl of at most 4 carbon atoms.

Among the specific preferred products are 2-butyl 3-[(2'-1H-tetrazol 5-yl) (1,1'-biphenyl) 4-yl) methyl]pyrazolo-(1,5-a) pyridine 4-carboxylic acid, 4'-[(2-butyl pyrazolo-(1,5-a)pyridin 3-yl) methyl](1,1'-biphenyl) 2-carboxylic acid, 4'-[(2-butyl imidazo-(1,2-a)pyridin 3-yl) methyl](1,1'-biphenyl) 2-carboxylic acid, 4-[(2-butyl imidazo-(1,2-a) pyridin 3-yl) methyl]benzoic acid and their addition salts with mineral and organic acids or with mineral and organic bases.

The process for the preparation of the compound of formula $I_m$ which corresponds to the products of formula I, in which $R_5$ is

or methylene comprises reacting a compound of the formula

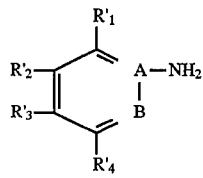

II in which A and B have the meaning above and $R'_1$, $R'_2$, $R'_3$ and $R'_4$ have the meanings above for $R_1$, $R_2$, $R_3$ and $R_4$ in which the optional reactive functions are optionally protected by protective groups with a compound of the formula

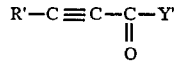

III in which R' and Y' have the meanings above for R and Y in which the optional reactive functions are optionally protected by protective groups to obtain a product of the formula

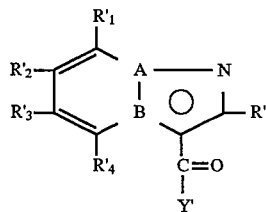

IV in which A, B, R', $R'_1$, $R'_2$, $R'_3$, $R'_4$ and Y' have the meanings above, optionally reducing the latter to obtain a product of the formula

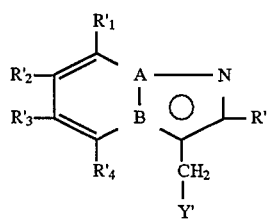

V in which R', $R'_1$, $R'_2$, $R'_3$, $R'_4$ and Y' have the meanings above and subjecting the compounds of formulae IV and V optionally and if necessary, to one or more of the following reactions in any order:

an elimination reaction of the protective groups that can be carried by the protected reactive functions, a salification reaction by a mineral or organic acid or by a base to obtain the corresponding salt, a hydrogenation reaction of the pyridinyl ring which carries the A and B groups, a substitution reaction of a halogen by cyano, a substitution reaction of a halogen by an optionally substituted alkyl or aryl, a conversion reaction of the cyano function into an acid function, a conversion reaction of the cyano function into a tetrazolyl function, an esterification or salification reaction of the acid function, a conversion reaction of the formyl into a carbamoyl, a conversion reaction of the carbamoyl into a cyano, a saponification reaction of the ester function into an acid function, a conversion reaction of the alkoxy function into a hydroxyl function, a reduction reaction of the carboxy function into an alcohol function, a reduction reaction of the oxo function into an alkylene, an oxidation reaction of the alkylene into an oxo function, a conversion reaction of the alkylthio or arylthio into corresponding sulfoxide or sulfone, a resolution reaction of the racemic forms into resolved products, the said products of formula $I_m$ thus obtained, which correspond to products of formula I as defined above in which $R_5$ is

or methylene, being in all possible racemic, enantiomeric and diastereoisomeric isomer forms.

Also the process for the preparation of compounds of formula I comprises reacting a compound of the formula

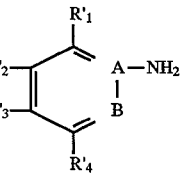

II in which A and B have the meaning above, and $R'_1$, $R'_2$, $R'_3$ and $R'_4$ have the meanings above respectively for $R_1$, $R_2$, $R_3$ and $R_4$ in which the optional reactive functions are optionally protected by protective groups with a compound of the formula

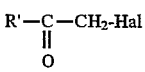

VI in which R' has the meaning above for R, in which the optional reactive functions are optionally protected by protective groups and Hal is halogen to obtain a product of the formula

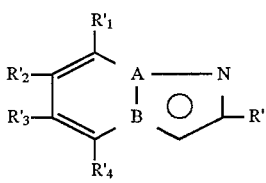

VII in which A, B, R', R'$_1$, R'$_2$, R'$_3$ and R'$_4$ have the meanings above, which is subjected to a halogenation reaction to obtain a product of the formula

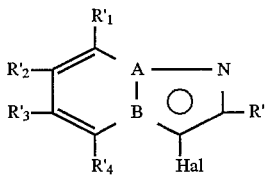

VIII in which A, B, R', R'$_1$, R'$_2$, R'$_3$ and R'$_4$ have the meanings above and Hal is halogen, reacting the latter with a compound of the formula $$Br-Zn-R_5-Y'$$      IX in which Y' has the meaning above for Y in which the optional reactive functions are optionally protected by protective groups and R$_5$ has the meaning indicated above to obtain a product of the formula

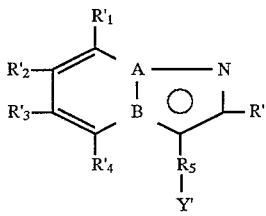

X in which A, B, R', R'$_1$, R'$_2$, R'$_3$, R'$_4$, R$_5$ and Y' have the meanings above and optionally subject to the latter, if desired and if necessary, to one or more of the following reactions in any order:

an elimination reaction of the protective groups that can be carried by the protected reactive functions, a salification reaction by a mineral or organic acid or by a base to obtain the corresponding salt, a hydrogenation reaction of the pyridinyl ring, a substitution reaction of halogen by cyano, a substitution reaction of halogen by an optionally substituted aryl, a conversion reaction of the cyano function into an acid function, a conversion reaction of the cyano function into a tetrazolyl function, an esterification or salification reaction of the acid function, a conversion reaction of the formyl into a carbamoyl, a conversion reaction of the carbamoyl radical into a cyano radical, a saponification reaction of the ester function into an acid function, a conversion reaction of the alkoxy function into a hydroxyl function, a reduction reaction of the carboxy function into an alcohol function, a reduction reaction of the oxo function into an alkylene, an oxidation reaction of the alkylene into an oxo function, a conversion reaction of the alkylthio or arylthio into corresponding sulfoxide or sulfone, a resolution reaction of the racemic forms into resolved products, the said products of formula I thus obtained being in all possible racemic, enantiomeric and diastereoisomeric isomer forms.

In the preferred conditions for the process of the invention:

the product of formula IV can be obtained by the addition of the compound of formula III onto the free amine function of the compound of formula II, followed by a cyclization reaction. This process applies to the formation of all the products of formula I, but preferably to the preparation of the products of formula I in which A is nitrogen and B is a carbon atom. The reaction to obtain the compound of formula IV can be described in the following manner:

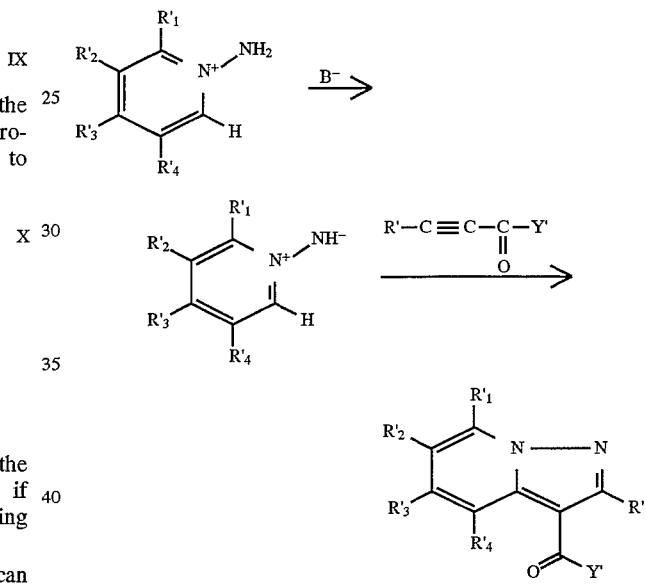

The reaction of the product of formula III on the product of formula II can be carried out in a solvent such as acetonitrile, dimethylformamide or tetrahydrofuran, dimethoxyethane or dimethylsulfoxide at reflux or at ambient temperature, preferably with stirring. The reaction is carried out in the presence of a base such as sodium or potassium hydride or sodium or potassium carbonate, sodium or potassium methylate or ethylate or tert-butylate.

The oxo function of the products of formula IV can be reduced to methylene to give the products of formula V, under known conditions, such as in the presence of hydrogen and palladium in a solvent such as acetic acid, perchloric acid, or in the presence of lithium aluminium hydride in a solvent such as ethyl ether preferably in the presence of a Lewis acid such as aluminium chloride. Separation is carried out with hydrazine hydrate in the presence of potassium—carbonate in ethylene glycol at 140°–210° C., according to Wolff-Kishner.

In the compound of formula VI, the halogen may be chlorine or fluorine and preferably bromine. The addition reaction of the compound of formula VI on the compound of formula II to obtain the product of formula VII can be carried out in a solvent such as acetone at reflux. This reaction is preferred when the compound of formula II is such that A is a carbon atom and B is nitrogen.

The product of formula VII can be subjected to a halogenation reaction to give the product of formula VIII. In this reaction, the halogen can be chlorine or bromine, the bromination reaction can be carried out in the presence of N-bromo succinimide in a solvent such as chloroform.

The addition reaction of the compound of formula IX on the product of formula VIII can be carried out under the usual conditions, by the reaction of an organo metallic compound which can be a magnesium compound or a zinc-compound on halogen in a solvent such as tetrahydrofuran.

Depending upon the values of R', R'$_1$, R'$_2$, R'$_3$, R'$_4$ and Y', the products of formula IV, V and X may or may not be a product of formula I. The various reactive functions that can be carried by some of the reaction compounds defined above can, if necessary, be protected, for example hydroxyl, acyl, free carboxy or also amino and monoalkylamino can be protected by appropriate protective groups.

The following non-exhaustive list of examples of protection of the reactive functions can be mentioned hydroxyl can be protected by alkyl such as tert-butyl, trimethylsilyl, tert-butyldimethyl-silyl, methoxymethyl, tetrahydropyrannyl, benzyl or acetyl; amino can be protected by acetyl, trityl, benzyl, tert-butoxy-carbonyl, phthalimido or other groups known in the chemistry of the peptides; acyl such as formyl can be protected in the form of cyclic or non-cyclic ketals such as dimethyl or diethylketal or ethylene dioxyketal; acid functions can be, if desired, amidified by a primary or secondary amine for example in methylene chloride in the presence of 1-ethyl-3-(dimethylamino-propyl) carbodiimide hydrochloride at ambient temperature or acid functions can be protected in the form of esters formed with easily-cleavable esters such as methyl, ethyl, benzyl or ter butyl esters or esters known in the chemistry of the peptides.

The reactions to which the products of formula IV, V or X can be subjected, if desired or if necessary, can be carried out, for example, as indicated hereafter. The elimination of protective groups such as those indicated above can be carried out under the usual known conditions such as an acid hydrolysis carried out with an acid such as hydrochloric, benzene sulfonic or para-toluene sulfonic acid in a formic or trifluoroacetic alkanol or an alkaline with sodium hydroxide and potassium hydroxide or also by catalytic hydrogenation. The phthalimido can be eliminated by hydrazine.

A list of the different protective groups which can be used will be found for example in the Patent BF 2 499 995.

The products can, if desired, be subjected to salification reactions by a mineral or organic acid by known methods. The products can, if desired, be subjected to salification reactions on the optional carboxy functions, by a mineral or organic base or to esterification reactions which can be carried out by known methods. The optional conversions of the ester functions into acid functions can be, if desired, carried out in the usual conditions such as by acid or alkaline hydrolysis with sodium hydroxide or potassium hydroxide in an alcoholic medium such as in methanol or also by hydrochloric or sulfuric acid.

The optional cyano functions can be, if desired, converted into an acid function under the usual conditions by a double hydrolysis carried out in an acid medium such as in a sulfuric acid, glacial acetic acid and water mixture, preferably in equal proportions, or also in sodium hydroxide, ethanol and water mixture at reflux.

The optional free or esterified carboxy functions can be, if desired, reduced to an alcohol function by known methods and the optional esterified carboxy functions can be, if desired, reduced to an alcohol function by known methods such as by lithium aluminium hydride in a solvent such as tetrahydrofuran or dioxane or ethyl ether.

The optional free carboxy functions of the products described above can be, if desired, reduced to alcohol functions with boron hydride. The optional alkoxy functions such as methoxy of the products described above can be, if desired, converted into a hydroxyl function by the usual conditions such as by boron tribromide in a solvent such as methylene chloride, by pyridine hydrobromide or hydrochloride or also by hydrobromic acid or hydrochloric acid in water or acetic acid at reflux.

The optional alkylthio or arylthio of the products can be, if desired, converted into the corresponding sulfoxide or sulfone functions by the usual conditions such as by peracids such as peracetic acid or metachloroperbenzoic acid or by ozone, oxone, sodium periodate in a solvent such as methylene chloride or dioxane at ambient temperature.

The obtaining of the sulfoxide function can be favoured by an equimolar mixture of the product containing an alkylthio or arylthio and the reagent may be a peracid. The obtaining of the sulfone function can be favoured by a mixture of the product with an alkylthio or arylthio with an excess of the reagent such as a peracid.

The substitution reaction of halogen by cyano can be carried out in the usual conditions, preferably by reaction of cuprous cyanide at reflux of dimethylformamide.

The hydrogenation of the pyridinyl ring can be carried out by the usual known methods by catalytic hydrogenation in the presence of palladium in an acetic acid and perchloric acid mixture or also of platinum oxide in acetic acid. The substitution of halogen by an optionally substituted aryl can be carried out under the usual conditions known to a man skilled in the art and notably by a metal, magnesium-compound or zinc-compound or organotin compound derivative on a bromine as indicated hereafter in the experimental part.

The oxidation of the alkylene into oxo can be carried out under the usual conditions and the reduction of the oxo function to an alkylene radical can be carried out by known methods described for the obtaining of products of formula V from the products of formula IV.

The optional alcohol functions of the products can be, if desired, converted into an aldehyde or acid function by oxidation under the usual conditions such as by the action of manganese oxide to obtain the aldehydes or by the action of Jones reagent to obtain the acids. The optional nitrile functions of the products can be, if desired, converted into tetrazolyl under the usual conditions by cycloaddition of a metal azide such as a trialkyltin azide on the nitrile function as indicated in the method described in J. Organometallic Chemistry., Vol. 33, 337 (1971) KOZIMA S., et al., The optional optically active forms of the products of formula I can be prepared by resolution of the racemics by known methods and the conversion reactions of formyl into carbamoyl and of carbamoyl into nitrile are carried out by known reaction. These reactions as well as the conversion of nitrile into tetrazole are carried out preferably when these substituents are carried in the alpha position of the biphenyl of —Y.

The compounds of formula I as well as their addition salts with acids have useful pharmacological properties. The products are endowed with antagonistic properties for the angiotensin II receptor and are inhibitors of the effects of angiotensin II, particularly of the vasoconstrictive effect and also of the trophic effect at the level of the myocytes. Some products also possess antagonistic properties for the endothelin receptor and are therefore antagonists of the vasoconstrictive effect of endothelin. The compounds of formulae Ib and I also possess the property of improving the cognitive functions.

A particular subject of the invention is, as medicaments, the products of formula I, in all possible racemic, enantiomeric and diastereoisomeric isomer forms, as well as their addition salts with pharmaceutically acceptable mineral and organic acids or mineral and organic bases.

Quite particularly a subject of the invention are the products of formula Ia and Ib in all possible racemic, enantiomeric and diastereoisomeric isomer forms, as well as their addition salts with pharmaceutically acceptable mineral and organic acids or mineral and organic bases.

The preferred compositions of the invention contain as the active ingredient at least one compound of the group consisting of 2-butyl 3-[(2'-1H-tetrazol 5-yl) (1,1'-biphenyl) 4-yl) methyl]pyrazolo-(1,5-a)pyridine 4-carboxylic acid, 4'-[(2-butyl pyrazolo-(1,5-a)pyridin 3-yl) methyl](1,1'-biphenyl) 2-carboxylic acid, 4'-[(2-butyl imidazo-(1,2-a)pyridin 3-yl) methyl](1,1'-biphenyl) 2-carboxylic acid, 4-[(2-butyl imidazo-(1,2-a)pyridin 3-yl) methyl]benzoic acid and their addition salts with pharmaceutically acceptable mineral or organic acids.

The compositions are useful in the treatment of cardiovascular illnesses causing a change in the vasomotricity: myocardial infarction, cardiac insufficiency, renal insufficiency, angina of the chest, cerebral vasospasm, Raynaud's disease, arterial hypertension and all illnesses resulting from an ischemia. They are also useful for the treatment of atherosclerosis, asthma and different types of visceral spasms, as well as as neuronal protective substances and in the prevention of the post-angioplasty recurrence of stenosis or also of glaucoma. They can also be used in the treatment of some gastro-intestinal, gynaecological disorders and especially for a relaxing effect at the level of the uterus as well as in the treatment of memory disorders, senile dementia and Alzheimer's disease.

The pharmaceutical compositions can be administered buccally, rectally, parenterally or as a topical application on the skin and mucous membranes.

The compositions can be solid or liquid and are in the pharmaceutical forms used in human medicine, such as tablets, dragees, capsules, granules, suppositories, injectable preparations, ointments, creams, gels and aerosol preparations.

The active ingredient can be incorporated with excipients usually employed in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, depending on the product used, the patient treated and the illness in question, can be 0.013 to 1.33 mg/Kg daily for an adult.

The starting compounds of formulae II, III, VI and IX are commercially available or can be prepared according to known methods.

Among the compounds of formula II which can be found commercially, are methyl metaaminobenzoate marketed for example by LANCASTER. Orthonitroaniline can also be mentioned in the form of a product marketed by UCB.

The compounds of formula VI can be haloketones and notably bromoketones.

Among the examples of the preparation of such compounds of formula VI described in the literature are J. Hel. Chem., Vol. 20, p. 623–628 (1983) and Liebigs Ann. Chem., Vol. 697, p. 62–68 (1966).

The compounds of formula III can be acetylene derivatives. Among the examples of the preparation of such compounds of formula III described in the literature are J. Am. Chem. Soc. 1937, Vol.59, p. 1490, and Synthesis 1977, p. 777.

Some products of formula IX which are not commercially available can be prepared by reacting a compound of the formula

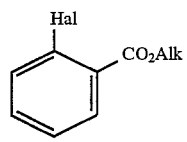

in which Alk and Hal are defined as above, with a compound of the formula $IX_b$

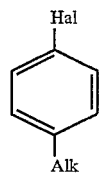

in which Alk and Hal have the meaning indicated above in the presence of copper powder at a temperature of approximately 100° C. to 300° C., to obtain a product of the formula

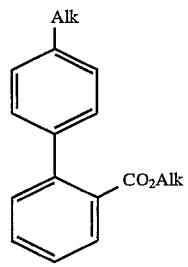

in which Alk has the meanings indicated above and optionally subjecting the esterified carboxy, if desired, to various known reactions to free the alkyl by standard methods or as indicated above, for example by acid or alkaline hydrolysis into cyano, tetrazole, arylalkyl by the usual methods and those described above by subjection to a bromination reaction on alkyl by standard methods by the action of n-bromosuccinimide in carbon tetrachloride and to the preparation of the corresponding organo metal compound such as a bromozinc compound to obtain a compound of the formula $BrZnR_5Y'$ IX.

Examples of the preparation of the compounds of formula IX are described in the literature and examples are given notably in U.S. Pat. No. 4,880,804 or Chemistry and Industry, 7th Sep. 1987, HOWARD et al., pp. 612–617.

Finally, the new intermediate products are those of formulae IV, V, VIII, IX and X.

In the following examples, there are described several preferred embodiments to illustrate the invention. However, it is to be understood that the invention is not intended to be limited to the specific embodiments.

EXAMPLE 1

(4-bromophenyl)(2-butylpyrazolo(1,5-a)pyridin-3-yl) methanone

Stage A: 1-(4-bromophenyl) 2-heptyn-1-one

The following were stirred at ambient temperature for about 2 hours 30 minutes, 49 ml of 1-hexyne, 75 ml of triethylamine, 40 mg of cuprous iodide, 40 mg of bis triphenylphosphine palladium dichloride and 9 g of parabromobenzoyl chloride.

The reaction mixture was taken up in water and ethyl acetate, filtered and extracted with ethyl acetate. After drying and filtering, the solvents were eliminated under reduced pressure at a temperature of about 50° C. to obtain after chromatography on silica (essence G: 90/ethyl acetate: 10), 7.63 g of the expected product.

Analyses

IR Spectrum ($CDCl_3$) —C≡C—2245 $cm^{-1}$ 2230 $cm^{-1}$ 2205 $cm^{-1}$ —C=O 1643 $cm^{-1}$ aromatics 1585 $cm^{-1}$–1570 $cm^{-1}$ 1482 $cm^{-1}$ Stage B: (4-bromophenyl)(2-butylpyrazolo(1,5-a)pyridin-3-yl) methanone A mixture of 2.5 g of N-aminopyridinium mesitylene sulfonate (prepared by Synthesis, 1977 page 1, TAMURA, et al.), 25 ml of acetonitrile and 3.5 g of potassium carbonate was stirred for 15 minutes at ambient temperature and then the 2.27 g of the product of Step A in solution in 25 ml of acetonitrile were added.

The mixture was stirred for 24 hours at ambient temperature and then refluxed for 3 hours. After chromatography on silica (essence G: 80/ethyl acetate: 20), the product was filtered, dried, impasted in ether, filtered and dried under reduced pressure to obtain 1.9 g of the expected product melting at 84° C.

Analyses $C_{18}H_{17}BrN_2O$; molecular weight=357.26

|  | C | H | Br | N | O |
|---|---|---|---|---|---|
| % calculated | 60.52 | 4.80 | 22.37 | 7.84 | 4.48 |
| % found | 60.7 | 4.8 | 22.1 | 7.8 |  |

IR Spectrum ($CHCl_3$) —C=O 1638 $cm^{-1}$ aromatics and heteroaromatics 1620 $cm^{-1}$–1589 $cm^{-1}$ 1567 $cm^{-1}$—1539 $cm^{-1}$ 1509 $cm^{-1}$

EXAMPLE 2

4-[(2-butylpyrazolo(1,5-a)pyridin-3-yl)carbonyl benzonitrile

A mixture of 1.5 g of the product of Example 1, 100 ml of dimethylformamide and 3 g of cuprous cyanide was refluxed for 24 hours and the reaction mixture was taken up in 400 ml of water and 400 ml of ethyl acetate, filtered and extracted with ethyl acetate. After drying and filtering, the solvents were eliminated under reduced pressure at a temperature of about 60° C. to obtain after chromatography on silica (essence G: 80/ethyl acetate: 20) 1.03 g of the expected product melting at 116° C.

Analyses

IR Spectrum ($CDCl_3$) —C≡N 2230 $cm^{-1}$ —C=O 1635 $cm^{-1}$ aromatics and heteroaromatics 1560 $cm^{-1}$–1540 $cm^{-1}$ 1508 $cm^{-1}$

EXAMPLE 3

4-[(2-butylpyrazolo(1,5-a)pyridin-3-yl)carbonyl] benzoic acid

A mixture of 845 mg of the product of Example 2 and 15 ml of a mixture in equal proportions of sulfuric acid, acetic acid and water was refluxed for 2 hours and the mixture was cooled down, taken up in water, filtered, washed with water and dried at 80° C. under reduced pressure.

The product was dissolved in acetonitrile at reflux, filtered hot, followed by concentration, ice-cooling, filtering and drying at 80° C., under reduced pressure to obtain 850 mg of the expected product melting at 196° C.

Analyses $C_{19}H_{18}N_2O_3$; molecular weight=322.37

|  | C | H | N |
|---|---|---|---|
| % calculated | 70.79 | 5.63 | 8.69 |
| % found | 71.0 | 5.7 | 8.4 |

IR Spectrum ($CDCl_3$) —C=O 1708 $cm^{-1}$ 1628 $cm^{-1}$ aromatic 1610 $cm^{-1}$–1595 $cm^{-1}$ 1570 $cm^{-1}$–1540 $cm^{-1}$ 1504 $cm^{-1}$

EXAMPLE 4

4-[(2-butyl4,5,6,7-tetrahydropyrazolo(1,5-a)pyridin-3-yl)methyl]benzoic acid

The following were hydrogenated at ambient temperature for about 30 minutes 437 mg of the product of Example 3 in 25 ml of acetic acid and 5 ml of perchloric acid in the presence of 200 mg of palladium at 10% on activated charcoal. Filtration was carried out and the filtrate was washed with ethyl acetate. 100 ml of water were added, followed by decanting and extraction with ethyl acetate. The extracts were dried, filtered and the solvents were eliminated at 50° C. under reduced pressure. The residue was dissolved in 50 ml of 1N sodium hydroxide and 20 ml of ether. The mixture was stirred, followed by decanting and extraction with 2×20 ml of 1N sodium hydroxide.

The product was acidified with concentrated hydrochloric acid and extracted with chloroform with 20% methanol and then the extracts were dried and filtered and the solvents were eliminated at 50° C. under reduced pressure. The resultant product was impasted in ether, followed by filtering and drying at 60° C. under reduced pressure. The purified product was obtained by dissolution in acetonitrile, operating as in Example 3, yielding 260 mg of the expected product melting at 148°–150° C.

Analyses $C_{19}H_{24}N_2O_2$; molecular weight=312.42

|  | C | H | N |
|---|---|---|---|
| % calculated | 73.05 | 7.74 | 8.97 |
| % found | 73.3 | 7.8 | 9.0 |

IR Spectrum ($CDCl_3$) absence of conjugated ketone —C=O 1725 $cm^{-1}$ (eq) 1892 $cm^{-1}$ (max) heterocycle and aromatic 1610 $cm^{-1}$–1575 $cm^{-1}$ 1560 $cm^{-1}$–1510 $cm^{-1}$ 1478 $cm^{-1}$

EXAMPLE 5

3-[(4-bromophenyl)methyl]2-butylpyrazolo(1,5-a) pyridine 1.25 g of lithium aluminium hydride were suspended in 100 ml of ether and then 1.46 g of aluminium chloride were added.

3.7 g of the product obtained in Example 1 were then introduced at ambient temperature and the mixture was stirred at ambient temperature for about 2 hours. Tetrahydrofuran with 20% water was introduced at a temperature of about 0° to 10° C., and the mixture was taken up in water, filtered, decanted and extracted with ethyl acetate. The organic phase was dried, filtered and the solvents were eliminated under reduced pressure at a temperature of about 50° C. to obtain 3.7 g of the expected product melting at <50° C.

Analyses

IR Spectrum (CHCl$_3$) conjugated system and aromatics 1636 cm$^{-1}$–1542 cm$^{-1}$ 1488 cm$^{-1}$

EXAMPLE 6

1,1-dimethylethyl4'-[(2-butylpyrazolo(1,5-a)pyridin-3-yl)methyl]-(1,1'-biphenyl)2-carboxylate Stage A: 3-[(4-(tributyltin)phenyl)methyl]2-butylpyrazolo(1,5-a) pyridine 3.13 g of the product of Example 5, 30 ml of dimethylformamide, 13.8 ml of bis tributyltin and 640 mg of bis (triphenylphosphine palladium) dichloride (FLUKA) were mixed together and the mixture was heated to 120° C. for 30 minutes, then taken up in water and extracted with ethyl acetate. The solvents were eliminated under reduced pressure and the residue was purified by chromatography on silica (elution essence G: 80/ethyl acetate: 20) to obtain 2.6 g of the expected product.

Stage B: 1,1-dimethylethyl4'-[(2-butylpyrazol(1,5-a) pyridin-3-yl) methyl](1,1'-biphenyl) 2-carboxylate 2.6 g of the product of Step A, 1.52 g of 1,1-dimethylethyl 2-benzoate iodide, 30 ml of toluene and 350 mg of bis (triphenylphosphine palladium) dichloride were mixed together and the mixture refluxed for 3 hours and then filtered and the solvent was driven off under reduced pressure. After chromatography on silica (first in methylene chloride then in an essence G: 80/ethyl acetate: 20 mixture), 1.055 g of expected product was obtained.

IR Spectrum (CHCl$_3$)

1703 cm$^{-1}$ 1368 cm$^{-1}$ aromatics and heteroaromatics 1636 cm$^{-1}$–1598 cm$^{-1}$ 1540 cm$^{-1}$–1492 cm$^{-1}$

EXAMPLE 7

4'-[(2utylpyrazolo(1,5-a)pyridin-3-yl)methyl](1,1'-biphenyl)2-carboxylic acid

A mixture of 1 g of the product of Example 6, 20 ml of methylene chloride and 4 ml of trifluoroacetic acid was stirred at room temperature for 4 hours and the solvent and the reagent were eliminated at 30° C. under reduced pressure. The residue was taken up in a mixture of 40 ml of 1N sodium hydroxide and 20 ml of ether and extracted with 1N sodium hydroxide. The aqueous phase was acidified with concentrated hydrochloric acid and extracted with ether after saturation with sodium chloride. After drying and filtering, the solvent was eliminated at 50° C. under reduced pressure.

Using the procedure of Example 3 but by purifying in isopropyl ether, 620 mg of the expected product were obtained, melting at 163° C.

Analyses for C$_{25}$H$_{24}$N$_2$O$_2$=384.48

|  | C | H | N |
|---|---|---|---|
| % calculated | 78.10 | 6.29 | 7.29 |
| % found | 78.0 | 6.3 | 7.3 |

IR Spectrum (CDCl$_3$) OH approx. 3510 cm$^{-1}$ —C=O 1730 cm$^{-1}$ 1697 cm$^{-1}$ aromatics and heterocycles 1637 cm$^{-1}$ 1612 cm$^{-1}$ 1600 cm$^{-1}$ 1575 cm$^{-1}$ 1565 cm$^{-1}$ 1543 cm$^{-1}$ 1515 cm$^{-1}$ 1494 cm$^{-1}$ 1482 cm$^{-1}$

EXAMPLE 8

1,1-dimethylethyl4'-[(2-butyl4,5,6,7-tetrahydro pyrazolo(1,5-a)pyridin-3-yl)methyl](1,1-biphenyl)2-carboxylate The following were stirred under hydrogen at ambient temperature for a few minutes until absorption was complete:

220 g of the product of Example 6, 20 ml of acetic acid and 100 mg of 82% platinum dioxide. Filtration was carried out followed by extraction with ethyl acetate. The extracts were purified by chromatography on silica (essence G: 80/ethyl acetate: 20) to obtain 145 mg of the expected product.

Analyses

IR Spectrum (CHCl$_3$) —C=O 1704 cm$^{-1}$ conjugated system and aromatics 1612 cm$^{-1}$–1600 cm$^{-1}$ 1562 cm$^{-1}$–1509 cm$^{-1}$

EXAMPLE 9

4'-[(2-butyl4,5,6,7-tetrahydro-pyrazolo(1,5-a) pyridin-3-yl)methyl](1,1'-biphenyl)2-carboxylic acid A mixture of 118 mg of the product obtained of Example 8, 2 ml of methylene chloride and 0.5 ml of trifluoroacetic acid was stirred for 6 hours at ambient temperature.

The solvent and the reagent were eliminated under reduced pressure and the residue was taken up in a mixture of 50 ml of ether and 50 ml of 1N sodium hydroxide. The aqueous phase was decanted and acidified by the addition of hydrochloric acid and extracted with a solution of chloroform with 20% methanol.

The resultant product was impasted in acetonitrile and filtration was carried out, followed by drying at 80° C. under pressure to obtain 80 mg of the expected product melting at 162° C.

Analyses

C$_{25}$H$_{28}$N$_2$O$_2$; molecular weight=388.51

|  | C | H | N |
|---|---|---|---|
| % calculated | 77.29 | 7.26 | 7.21 |
| % found | 77.5 | 7.4 | 7.1 |

EXAMPLE 10 ethyl2-butyl3-(4-bromobenzoyl)pyrazolo(1,5-a) pyridine6-carboxylate

The following are agitated for 3 hours at ambient temperature:

A mixture of 13.8 g of ethyl 1-aminopyridinium 3-carboxylate 2,4,6-trimethylbenzenesulphonate (compound A) (Synthesis 1977, page 1, TAMURA, et al.), 150 ml of dimethylformamide, 5.7 g of potassium carbonate and 10 g of the product of Step A of Example 1 were stirred for 3 hours at room temperature and then 6.9 g of compound A and 2.85 g of potassium carbonate were added. The mixture was stirred for 2 hours. Then 6.9 g of compound A and 2.85 g of potassium carbonate were added and the mixture was stirred for 2 hours at ambient temperature. The mixture was taken up in water and extracted with ethyl acetate. Separation was carried out by chromatography on silica (essence G: 80/ethyl acetate: 20) to obtain 7.38 g of the expected product (M.p.$\leq$50° C.) and 8.25 g of the corresponding isomer of Example 16.

Analyses

IR Spectrum ($CHCl_3$) —C=O 1721 $cm^{-1}$ 1633 $cm^{-1}$ aromatics and heteroaromatics 1587 $cm^{-1}$–1565 $cm^{-1}$ 1541 $cm^{-1}$–1519 $cm^{-1}$

EXAMPLE 11

2-butyl3-[(4-bromophenyl)methyl]pyrazolo(1,5-a) pyridin6-carboxylic acid

A mixture of 6.6 g of the product of Example 10, 300 ml of ethylene glycol, 60 ml of a solution of 64% hydrazine hydrate and 10 ml of potassium hydroxide was heated for about 2 hours at a temperature of about 140° C., then for about 2 hours while distilling the water of the reaction mixture. After cooling, the solution was poured into 600 ml of water and ice, acidified by the addition of concentrated hydrochloric acid, stirred at 0° C., filtered and dried under reduced pressure at ambient temperature to obtain 4 g of the expected product.

EXAMPLE 12 methyl 2-butyl3-[(4-bromophenyl)methyl]pyrazolo (1,5-a)pyridin6-carboxylate 100 ml of a solution of diazomethane in methylene chloride were added at ambient temperature to a suspension of 4 g of the product of Example 11 in 100 ml of methylene chloride and the solvent was eliminated at 40° C. under reduced pressure. Chromatography on silica was carried out (hexane: 80/ethyl acetate: 20) to obtain 3.7 g of the expected product melting at < or=50° C.

IR Spectrum ($CHCl_3$) —C=O 1721 $cm^{-1}$ conjugated system and heteroaromatics 1635 $cm^{-1}$–1530 $cm^{-1}$

EXAMPLE 13 methyl 2-butyl3-[(2'-cyano(1,1'-biphenyl)4-yl) methyl]pyrazolo(1,5-a)pyridin6-carboxylate Stage A: methyl 2-butyl3-[(4-(tributyltinphenyl)methyl] pyrazolo(1,5-a)pyridine)6-carboxylate A mixture of 3.7 g of the product of Example 12, 35 ml of dimethylformamide, 13.2 ml of hexabutyldistannane (FLUKA) and 620 mg of bis (triphenylphosphine) palladium chloride was heated to 120° C. for one hour, then left for 30 minutes at ambient temperature. The mixture was taken up in water and extracted with ethyl acetate. The extracts were dried and evaporated to dryness and the residue was chromatographed on silica (hexane: 80/ethyl acetate: 20) to obtain 2.9 g of the expected product.

Stage B: methyl 2-butyl3-[(2'-cyano(1,1'-biphenyl)4-yl) methyl]pyrazolo(1,5-a)pyridin6-carboxylate A mixture of 2.9 g of the product of Step A, 950 mg of 2-bromobenzonitrile, 50 ml of toluene and 330 mg of bis (triphenylphosphine) palladium chloride was refluxed for 6 hours, then left for 16 hours at ambient temperature. After filtration, the solvent was eliminated under reduced pressure and the residue was chromatographed on silica (hexane: 80/ethyl acetate: 20). The solvent was eliminated under reduced pressure to obtain 1.625 g of the expected product.

IR Spectrum ($CHCl_3$) —C$\equiv$N 2226 $cm^{-1}$ —$CO_2Me$ 1720 $cm^{-1}$–1437 $cm^{-1}$ aromatics and heteroaromatics 1635 $cm^{-1}$–1613 $cm^{-1}$ 1598 $cm^{-1}$–1533 $cm^{-1}$

EXAMPLE 14 methyl 2-butyl3-[(2'-(1H-tetrazol-5-yl) (1,1'- biphenyl)4-yl) methyl]pyrazolo(1,5-a)pyridin6- carboxylate A mixture of 1.625 g of the product of Example 13, 20 ml of toluene and 800 mg of trimethyltin azide was refluxed for about 72 hours during which time 800 mg of trimethyltin azide were added each time at the end of about 16 hours and 48 hours. 20 ml of tetrahydrofuran were added and then hydrochloric gas was bubbled through for 30 minutes at ambient temperature. Then, the hydrochloric gas was eliminated by bubbling through nitrogen and the solvent was evaporated off under reduced pressure. Chromatography was carried out on silica (chloroform: 90/methanol: 10) and the solvents were eliminated under reduced pressure to obtain 1.35 g of the expected product.

Analyses

IR Spectrum (chloroform) =C—NH—3408 $cm^{-1}$ —C=O 1721 $cm^{-1}$ ($CO_2Me$) 1437 $cm^{-1}$ aromatics and heteroaromatics 1635 $cm^{-1}$–1604 $cm^{-1}$ 1579 $cm^{-1}$–1543 $cm^{-1}$ 1534 $cm^{-1}$–1515 $cm^{-1}$

EXAMPLE 15

2-butyl3[(2'-(1H-tetrazol-5-yl)(1,1'-biphenyl)4-yl) methyl]pyrazolo(1,5-a)pyridin6-carboxylic acid A mixture of 1.65 g of the product of Example 14, 80 ml of terbutyl alcohol and 40 ml of potassium hydroxide was refluxed for 2 hours.

The terbutanol was eliminated under reduced pressure and the mixture was diluted with about 250 ml of water, filtered and extracted with ether. The aqueous phase was acidified by the addition of concentrated hydrochloric acid with stirring at a temperature of about 0° to 5° C., and stood for 16 hours at ambient temperature, then was filtered and dried under reduced pressure. The product was dissolved in 300 ml of a water: 50/isopropanol: 50 mixture under reflux and the solution was filtered. The isopropanol was eliminated under reduced pressure, followed by ice-cooling, separating and drying to obtain 1 g of the expected product.

Analyses

IR Spectrum (NUJOL) —C=O 1697 $cm^{-1}$ conjugated system 1636 $cm^{-1}$–1603 $cm^{-1}$ 1534 $cm^{-1}$–1485 $cm^{-1}$

EXAMPLE 16 ethyl 2-butyl3-(4-bromobenzoyl)pyrazolo(1,5-a) pyridine4-carboxylate

This product was the isomer of the product of Example 10 which after separation by chromatography, 8.25 g of the expected product melting at <50° C. were obtained.

Analyses

IR Spectrum ($CHCl_3$) —C=O 1720 $cm^{-1}$ 1652 $cm^{-1}$ aromatics and heteroaromatics 1624 $cm^{-1}$–1586 $cm^{-1}$ 1569 $cm^{-1}$–1550 $cm^{-1}$ 1518 $cm^{-1}$

EXAMPLE 17

2-butyl3-[(4-bromophenyl)methyl]pyrazolo(1,5-a)pyridin4-carboxylic acid

Using the procedure of Example 11, a mixture of 6.75 g of the product of Example 16, 200 ml of ethylene glycol, 70 ml of a solution of 64% hydrazine hydrate and 10 ml of potassium hydroxide were reacted to obtain 11.16 g of the expected product which was used as is for the following example.

EXAMPLE 18 methyl 2-butyl3-[(4-bromophenyl)methyl]pyrazolo(1,5-a)pyridin4-carboxylate

Using the procedure of Example 12, 11.16 g of the product of Example 17 were reacted to obtain after chromatography on silica (hexane: 80/ethyl acetate: 20), 3.7 g of the expected product melting at 80°–85° C.

IR Spectrum (CHCl$_3$) —CO$_2$Me 1723 cm$^{-1}$ and 1439 cm$^{-1}$ conjugated system and heteroaromatics 1622 cm$^{-1}$–1590 cm$^{-1}$ 1560 cm$^{-1}$–1544 cm$^{-1}$

EXAMPLE 19 methyl 2-butyl3-[(2'-cyano(1,1'-biphenyl)4-yl)methyl]pyrazolo(1,5-a)pyridine4-carboxylate Stage A: methyl 2-butyl3-[(4-(tributyltinphenyl)methyl]pyrazolo(1,5-a)pyridine4-carboxylate Using the procedure of Stage A of Example 13, 4.5 g of the product of Example 18, 45 ml of dimethylformamide, 16.5 ml of hexabutyldistannane and 770 mg of bis(triphenylphosphine) palladium chloride were reacted to obtain 4.3 g of the expected product.

Stage B: methyl 2-butyl3-[(2'-cyano(1,1'-biphenyl)4-yl)methyl]pyrazolo(1,5-a)pyridine4-carboxylate Using the procedure of Stage B of Example 13, 4.3 g of the product of Stage A, 1.3 g of 2-bromobenzonitrile, 75 ml of toluene and 490 mg of bis(triphenylphosphine) palladium chloride were reacted to obtain 2.38 g of the expected product melting at 92°–95° C.

IR Spectrum (CHCl$_3$) —C≡N 2225 cm$^{-1}$ (F) —CO$_2$Me 1722 cm$^{-1}$–1439 cm$^{-1}$ aromatics and heteroaromatics 1622 cm$^{-1}$–1612 cm$^{-1}$ 1595 cm$^{-1}$–1570 cm$^{-1}$ 1555 cm$^{-1}$

EXAMPLE 20 methyl 2-butyl3-[(2'-(1H-tetrazol-5-yl)(1,1'-biphenyl)4-yl)methyl]pyrazolo(1,5-a)pyridin4-carboxylate Using the procedure of Example 14, 945 mg of the product of Example 19, 10 ml of toluene and 460 mg of trimethyltin azide were reacted to obtain after chromatography (chloroform: 80/methanol: 20), 1.02 g of the expected product.

EXAMPLE 21

2-butyl3-[(2'-(1H-tetrazol-5-yl)(1,1'-biphenyl)4-yl)methyl]pyrazolo(1,5-a)pyridin4-carboxylic acid Using the procedure of Example 15, 1.02 g of the product of Example 20, 50 ml of terbutyl alcohol and 25 ml of potassium hydroxide were reacted to obtain after recrystallization from acetonitrile, 686 mg of the expected product melting at 214° C.

Analyses C$_{26}$H$_{24}$N$_6$O$_2$; molecular weight=452.52

|  | C | H | N |
| --- | --- | --- | --- |
| % calculated | 69.01 | 5.35 | 18.57 |
| % found | 69.0 | 5.2 | 18.6 |

IR Spectrum (NUJOL) —C=O 1710 cm$^{-1}$ conjugated system and aromatics 1618 cm$^{-1}$–1606 cm$^{-1}$ 1580 cm$^{-1}$–1572 cm$^{-1}$ 1548 cm$^{-1}$–1530 cm$^{-1}$ 1496 cm$^{-1}$

EXAMPLE 22

3-[(4-cyanophenyl)methyl]2-butylimidazo(1,2-a)pyridine

Stage A: 1-bromo2-hexanol

A mixture of 8 ml of 1,2 epoxy hexane and 80 ml of acetonitrile was cooled down to 0° C. and 5.77 g of lithium bromide were added. 8.43 ml of trimethylchlorosilane were added at 0° C., agitation is carried out for 4 hours at 0° C., followed by filtration. The filtrate was washed with ethyl acetate, poured into 150 ml of 1N hydrochloric acid and stirred for 15 minutes. After chromatography (methylene chloride: 30/hexane: 70), the organic phase was washed with water saturated in sodium chloride, dried, filtered and distilled to obtain 10.22 g of the expected product in the form of a colourless oil.

Stage B: 1-bromo2-hexanone

A mixture of 30 g of the product of Stage A and 120 ml of anhydrous acetone was cooled to 0° C. and while maintaining this temperature, 49.5 ml of Jones reagent were added dropwise. The mixture was stirred for 90 minutes and a saturated aqueous solution of sodium chloride was poured into the solution which had returned to ambient temperature. The mixture was extracted with ethyl acetate and the organic phase was washed with water, dried, filtered and distilled to obtain after chromatography (methylene chloride) 13.8 g of the expected product in the form of a colourless oil.

Analyses

IR Spectrum (NUJOL) —C=O 1730 cm$^{-1}$ —C=O 1714 cm$^{-1}$

Stage C: 2-butylimidazo(1,2-a)pyridine

A mixture of 6 g of 2-amino pyridine and 60 ml of anhydrous acetone was added to a mixture of 16 g of the product of Stage B and 20 ml of acetone at ambient temperature. The mixture was refluxed for one hour and the acetone was partially distilled. The mixture was allowed to return to ambient temperature, ice-cooled, separated and washed with ethyl ether. The insoluble part was dissolved in a saturated solution of sodium carbonate and extraction was carried out with ethyl acetate. The extracts were washed with water saturated in sodium chloride, dried and filtered to obtain 5.9 g of the expected product in the form of a yellow oil.

Analyses

IR Spectrum (CHCl$_3$) conjugated system and aromatics 1638 cm$^{-1}$–1610 cm$^{-1}$ 1492 cm$^{-1}$ Stage D: 3-bromo2-butylimidazo(1,2-a)pyridine A mixture of 3.5 g of the product of Stage C and 50 ml of chloroform was cooled to 10° C. and 4.55 g of N-bromo succinimide were added. The mixture was stirred at this temperature for 30 minutes and was then poured into a saturated solution of sodium carbonate and extracted with ethyl acetate. The extracts, were washed with a saturated aqueous solution of sodium chloride, dried, filtered and evaporated to dryness to obtain after chromatography on silica (methylene chloride: 95/methanol: 5), 3.8 g of the expected product in the form of a black oil.

Analyses

IR Spectrum (CHCl$_3$) heterocycles 1632 cm$^{-1}$–1603 cm$^{-1}$ 1529 cm$^{-1}$–1499 cm$^{-1}$ Stage E: 4-[(2-butylimidazo(1,2-a)pyridine3-yl)methyl]benzonitrile A mixture of 2 g of the product of Stage D, 100 ml of tetrahydrofuran and 1 g of [tetra-bis(triphenylphosphine)]palladium was added to 35.9 ml of zinc 4-bromomethyl benzonitrile at ambient temperature and the mixture was refluxed for one hour. The mixture was allowed to return to ambient temperature, poured into water and extracted with ethyl acetate. The extracts were washed with a saturated aqueous solution of sodium chloride, dried, filtered and brought to dryness to obtain after chromatography on silica (ethyl acetate), 1.1 g of the expected product.

Analyses

IR Spectrum (CHCl$_3$) —C≡N 2232 cm conjugated system and aromatics 1636 cm$^{-1}$–1608 cm$^{-1}$ 1560 cm$^{-1}$–1504 cm$^{-1}$

EXAMPLE 23

4-[(2-butylimidazo(1,2a)pyridin3-yl)methyl]benzoic acid hydrochloride a) 4-[(2-butylimidazo(1,2-a)pyridin3-yl)methyl]benzoic acid A mixture of 0.270 g of the product of Example 22, 2.7 ml of sodium hydroxide and 1 ml of ethanol was refluxed for about 5 hours.

100 ml of water were poured into the solution which had returned to ambient temperature and acidification was carried out by bubbling through SO$_2$ until the pH=2. Extraction was carried out with ethyl acetate and the organic phase was dried, filtered and brought to dryness to obtain after chromatography on silica (methylene chloride: 90/methanol: 10), 0.51 g of expected product is obtained.

b) 4-[(2-butylimidazo(1,2-a)pyridin-3-yl)methyl]benzoic acid hydrochloride

A mixture of 0.3 g of the product of Stage A, 10 ml of ethanol and 6.6 ml of 6.6N hydrochloric acid in ethanol was filtered and 25 ml of ether were added, followed by ice-cooling, separation and drying under reduced pressure at 80° C.

8 ml of isopropanol were added, followed by filtration, ice-cooling, separation, washing with 2 ml of isopropanol then with diethyl oxide and drying under reduced pressure at 60° C. to obtain 0.0586 g of the expected product melting at 244° C.

Analyses

IR Spectrum (NUJOL) C=O 1715 cm$^{-1}$ aromatics and heterocycle 1614 cm$^{-1}$–1575 cm$^{-1}$ 1508 cm$^{-1}$

EXAMPLE 24 methyl 4'-[(2-butylimidazo(1,2-a)pyridine3-yl)methyl](1,1'-biphenyl)2-carboxylate A mixture of 0.290 g of electrolytic zinc, 0.41 g of [tetra-bis(triphenylphosphine)]palladium and 1.36 g of methyl bromomethyl-(1,1'-biphenyl) 2-carboxylate was dried under reduced pressure and 0.75 g of the product of Stage D of Example 22 and 22 ml of tetrahydrofuran were added under a nitrogen atmosphere. The mixture was taken to 65° C. for one hour and 0.3875 g of electrolytic zinc and 1.81 g of methyl bromomethyl (1,1'-biphenyl) 2-carboxylate were added. The mixture was refluxed for 18 hours and the resultant mixture was poured into a saturated solution of sodium carbonate and extracted with ethyl acetate. The extracts were washed with water saturated with sodium chloride, dried, filtered and evaporated to dryness to obtain after chromatography (ethyl acetate), 0.500 g of the expected product.

Analyses

IR Spectrum (CHCl$_3$) (chloroform) C=O 1722 cm$^{-1}$ aromatics and heterocycle 1638 cm$^{-1}$–1600 cm$^{-1}$ 1565 cm$^{-1}$–1508 cm$^{-1}$

EXAMPLE 25

4'-[(2-butylimidazo(1,2-a)pyridine3-yl)methyl](1,1'-biphenyl)2-carboxylic acid

A mixture of 0.500 g of the product of Example 24, 1.5 ml of ethanol and 1.5 ml of sodium hydroxide was refluxed for one hour.

100 ml of water were poured into the solution which had returned to ambient temperature. Acidification was carried out by bubbling through SO$_2$ until the pH=2, followed by extraction with ethyl acetate. The organic phase was dried, filtered and evaporated to dryness. The residue was impasted in 15 ml of acetone, 6.6 ml of ethanol were added, followed by filtration, separation and drying under reduced pressure at 80° C. to obtain 0.202 g of the expected product melting at 196° C.

Analyses

IR Spectrum (NUJOL) C=O 1674 cm$^{-1}$ conjugated system and aromatics 1599 cm$^{-1}$–1574 cm$^{-1}$ 1560 cm$^{-1}$14 1504 cm$^{-1}$

EXAMPLE 26

4-[(2-methylimidazo(1,2-a)pyridin3-yl)methyl]benzonitrile hydrochloride

Stage A: 2-methylimidazo(1,2-a)pyridine

A mixture of 5 g of 2-amino pyridine and 250 ml of acetone were added at ambient temperature to a mixture of 7.25 g of 1 bromo 2-propanone and 20 ml of acetone and the mixture was refluxed for 30 minutes. Using the procedure of Stage C of Example 22, 5.3 g of the expected product were obtained in the form of an orange oil.

Analyses

IR Spectrum (NUJOL) conjugated system 1638 cm$^{-1}$–1602 cm$^{-1}$ 1549 cm$^{-1}$–1509 cm$^{-1}$ Stage B: 3-bromo2-methylimidazo(1,2-a)pyridine A mixture of 5.3 g of the product of Stage A and 150 ml of chloroform was cooled to 10° C. and 7.5 g of N-bromo succinimide were added. The mixture was stirred for 30 minutes at 10° C.

Using the procedure of Stage D of Example 22, 7.47 g of the expected product melting at 70° C. were obtained.

Stage C: 4-[(2-methylimidazo(1,2-a)pyridin3-yl)methyl]benzonitrile.

A mixture of 3.9 g of the product of Stage B, 24 ml of tetrahydrofuran and 2.57 g of [tetra-bis(triphenylphosphine)]palladium were stirred at ambient temperature and 77.8 ml of zinc 4-bromomethyl benzonitrile were added. The mixture was refluxed for 2 hours.

It was poured into a saturated solution of sodium bicarbonate and extracted with ethyl acetate. The extracts were washed with water saturated with sodium chloride, dried, filtered and dried to obtain after chromatography (methylene chloride: 95/methanol: 5), 5 g of the expected product.

Stage D: 4-[(2-methylimidazo(1,2-a)pyridin 3-yl)methyl] benzonitrile hydrochloride.

A mixture of 5 g of the product of Stage C, 80 ml of ethyl acetate and 3.5 ml of 6.6N hydrochloric acid in ethanol was ice-cooled, separated, washed with ethyl acetate and dried under reduced pressure at 80° C. to obtain 5 g of the expected product melting at 230° C.

Analyses

IR Spectrum (NUJOL) C≡N 2230 $cm^{-1}$ aromatics and conjugated system 1638 $cm^{-1}$–1610 $cm^{-1}$ 1570 $cm^{-1}$–1504 $cm^{-1}$

EXAMPLE 27

4-[(2-methylimidazo(1,2-a)pyridin3-yl)methyl] benzoic acid

A mixture of 2.6 g of the product of Example 26 and 150 ml of sodium hydroxide was refluxed for about 8 hours.

The mixture was allowed to return to ambient temperature and was poured into a saturated aqueous solution of sodium dihydrogeno-phosphate (pH=4) and extracted with 6×300 ml of ethyl acetate. The organic phase was dried and filtered and 55 ml of isopropanol were added, followed by filtration, ice-cooling, separation, washing with 5 ml of isopropanol then with ethyl ether and drying under reduced pressure at 100° C. to obtain 0.410 g of the expected product melting at 217° C.

Analyses

IR Spectrum (NUJOL) C=O 1698 $cm^{-1}$ conjugated system and aromatics 1612 $cm^{-1}$–1578 $cm^{-1}$ 1506 $cm^{-1}$

EXAMPLE 28

(4-bromophenyl)(2-butyl7-methylpyrazolo(1,5-a) pyridin-3-yl)methanone

A mixture of 11.4 g of the product of Stage A of Example 1, 250 ml of dimethylformamide and 9.81 g of 1-amino 2-methylpyridinium 2,4,6-trimethyl-benzene sulfonate (Synthesis, 1977, page 1, TAMURA, et al.) and 5.11 g of potassium carbonate were stirred for 5 hours at ambient temperature.

Then, the mixture was taken up in 200 ml of water and 200 ml of ethyl acetate, washed with salt water and evaporated to dryness under reduced pressure at 40° C.

The residue was chromatographed on silica (essence G: 80/ethyl acetate: 20), impasted in ether, followed by filtration and crystallization from acetonitrile to obtain 6.66 g of the expected product melting at 118° C.

Analyses

IR Spectrum (CHCl₃) —C=O 1636 $cm^{-1}$ Aromatics and heteroaromatics 1584 $cm^{-1}$–1554 $cm^{-1}$ 1516 $cm^{-1}$

EXAMPLE 29

3-[(4-bromophenyl)methyl]2-butyl7-methylpyrazolo (1,5-a)pyridine

A mixture of 100 ml of anhydrous ether and 0.924 g of lithium aluminium hydride was reacted with 1.08 g of aluminium chloride added slowly and a solution of 3 g of the product of Example 28 in 100 ml of ether was added dropwise. The mixture was stirred for 2 hours at ambient temperature.

Using the procedure of Example 5, 2.8 g of the expected product melting at 54° C. were obtained.

Analyses

IR Spectrum (CHCl₃) aromatic conjugated system 1639 $cm^{-1}$–1557 $cm^{-1}$

EXAMPLE 30

4'-[(2-butyl7-methylpyrazolo(1,5-a)pyridin3-yl) methyl](1,1'-biphenyl)2-carbonitrile Stage A: 2-butyl7-methyl3-[(4-(tributyltin)phenyl) methyl]pyrazolo(1,5-a)pyridine Using the procedure of Stage A of Example 13, 0.705 g of the product of Example 29, 8 ml of dimethylformamide, 3 ml of hexabutyldistannane (FLUKA) and 143 mg of bis (triphenylphosphine) palladium chloride were reacted to obtain after chromatography on silica (essence G: 90/ethyl acetate: 10), 0.734 g of the expected product.

IR Spectrum (CHCl₃) aromatics and conjugated system 1640 $cm^{-1}$–1590 $cm^{-1}$ 1558 $cm^{-1}$–1498 $cm^{-1}$ Stage B: 4'-[(2-butyl7-methylpyrazolo(1,5-a)pyridin3-yl) methyl](1,1'-biphenyl)2-carbonitrile Using the procedure of Stage B of Example 13, 0.734 g of the product of Stage A, 285 mg of 2-bromobenzonitrile, 10 ml of toluene and 100 mg of bis(triphenylphosphine) palladium chloride were reacted to obtain after chromatography on silica (eluant hexane-ethyl acetate 80–20), 156 mg of the expected product.

IR Spectrum (CHCl₃) —C≡N 2225 $cm^{-1}$ aromatics and heteroaromatics 1638 $cm^{-1}$–1612 $cm^{-1}$ 1598 $cm^{-1}$–1555 $cm^{-1}$ 1515 $cm^{-1}$–1500 $cm^{-1}$ 1477 $cm^{-1}$ and 74 mg of the product corresponding to Example 31.

EXAMPLE 31

3,3'-[[(1,1'-biphenyl)4,4'-diyl]bis-methyl]bis2-butyl 7-methylpyrazolo(1,5-a)pyridine The product of Example 31 was obtained by chromatographic separation of Example 30, and 74 mg of the expected product were obtained.

Analyses

IR Spectrum (CHCl₃), aromatics and heteroaromatics 1638 $cm^{-1}$–1610 $cm^{-1}$ 1555 $cm^{-1}$–1498 $cm^{-1}$

EXAMPLE 32

2-butyl7-methyl3-[[2'-(1H-tetrazol-5-yl)(1,1'-biphenyl)4-yl]methyl]pyrazolo(1,5-a)pyridine Using the procedure of Example 14, 0.258 g of the product of Example 31, 6 ml of toluene and 0.143 mg of trimethyltin nitride was stirred for 5 days after which 6 ml of tetrahydrofuran were added. Then hydrochloric gas was bubbled through for 30 minutes and then nitrogen was bubbled through for one hour. The mixture was diluted with water and extracted with ethyl acetate. The combined organic phases were washed with salt water, dried and the solvents were eliminated under reduced pressure at 50° C. The residue was taken up in acetonitrile to obtain 100 mg of the expected product.

Analyses

IR Spectrum (chloroform) conjugated system and aromatic 1636 $cm^{-1}$–1606 $cm^{-1}$ 1580 $cm^{-1}$–1508 $cm^{-1}$

EXAMPLE 33 of a pharmaceutical composition

Tablets were prepared corresponding to the following formula:

| | |
|---|---|
| Product of Example 21 | 10 mg |
| Excipient for a tablet completed at | 100 mg |

(detail of the excipient: lactose, talc, starch, magnesium stearate).

PHARMACOLOGICAL RESULTS

1 - Test on the angiotensin II receptor

A fresh membrane preparation obtained from the liver of a rat was used. The tissue was ground in a polytron in a Tris 50 mM pH 7.4 buffer and the grinding is followed by 3 centrifugings at 30,000 g for 15 minutes with intermediate taking up of the pellets in the Tris pH 7.4 buffer.

The last pellets were suspended in an incubation buffer (Tris 20 mM, NaCl 135 mM, KCl 10 mM, glucose 5 mM, $MgCl_2$ 10 mM, PMSF 0.3 mM, bacitracin 0.1 mM, BSA 0.2%).

2 ml aliquot fractions were distributed in hemolysis tubes and $^{125}$I angiotensin II (25,000 DPM/tube) and the product to be studied were added. The product was first tested with $3 \times 10^{-5} M$ in triplicate. When the tested product displaced more than 50% of the radioactivity bound specifically to the receptor, it was tested again according to a range of 7 concentrations to determine the concentration which inhibited by 50% the radioactivity bound specifically to the receptor. In this way, the 50% inhibiting concentration was determined.

The non-specific bond was determined by the addition of the product of Example 94 of the European Patent 0253310, at $10^{-5}M$ (in triplicate). The product was incubated at 25° C. for 150 minutes, put in a water-bath at 0° C. for 5 minutes, filtered under vacuum, rinsed with Tris pH 7.4 buffer and the radioactivity was counted in the presence of scintillating Triton.

The result was expressed directly as a 50% inhibiting concentration ($IC_{50}$), that is to say as the concentration of studied product, expressed in nM, necessary to displace 50% of the specific radioactivity fixed to the receptor studied.
Results:

| Product of Example | $IC_{50}$ in nanomoles |
|---|---|
| 21 | 0.5 |
| 32 | 24.0 |

2 - Test for antagonistic activity of angiotensin II in a demedullated rat

Male Sprague-Dawley rats (250 to 350 g) were anaesthetized by an intra-peritoneal injection of sodium pentobarbital (60 mg/kg). The diastolic arterial pressure was recorded using a heparinated catheter (PE50) introduced into the left carotid artery of the animal, and connected to a pressure processor (Gould, Pressure Processor) by means of a Gould pressure sensor.

A catheter was introduced into the right jugular vein of the animal to permit the injection of the molecules to be studied. The animal was placed under assisted respiration. A bilateral section of the pneumogastric nerve is carried out. The rat is then demedullated.

After a sufficient period of stabilization, the study of the antagonism of the molecules vis-a-vis angiotensin II (Hypertensin, CIBA) was carried out in the following way:

1 - Three consecutive injections of angiotensin II (0.75 micrograms/kg) at 15 minute intervals enabled a reproducible and stable pressure response to be obtained.

b 2- While keeping an administration frequency of 15 minutes of the angiotensin II, the molecules (0.01 to 10 mg/kg) were injected 5 minutes before the angiotensin II.

The effects on pressure of angiotensin II in the presence of the antagonist were expressed as a percentage of the effects on pressure of angiotensin II administered on its own. The dose inhibiting the studied effect by 50% was determined in this way ($ID_{50}$).

Each animal was considered as its own control.
Results:

| Product of Example | $ID_{50}$ in mg/kg |
|---|---|
| 21 | 0.3 |

3 - Test of the antagonistic activity of angiotensin II by oral route in a demedullated rat Male Sprague Dawley rats of equal weight (300–330 g) were selected. The animals were divided into several groups ($n \geq 6$ per group), receiving either the solvent (control group) or the antagonistic molecule of angiotensin II. The doses administered were determined from the $ID_{50}$ IV. The solvent used was methyl cellulose (5 ml/kg).

45 minutes after force-feeding, the animals were anaesthetized with sodium pentobarbital (60 mg/kg, IP). The diastolic arterial pressure was recorded using a heparinated catheter (PE50) introduced into the left carotid artery of the animal, and connected by means of a pressure sensor (Gould, P10 EZ) to a pressure processor (Gould, Pressure Processor). The rat was put under assisted respiration, then demedullated and bilaterally vagotomized.

Two injections of angiotensin II (0.75 ug/kg; Hypertensin, Ciba) were given via the pudendal vein, 60 and 75 minutes respectively after the force-feeding of the animals.

The effects on pressure of angiotensin II in the presence of the antagonist were expressed as a percentage of the effects on pressure of angiotensin II administered to the control group.

For each product, the dose inhibiting the studied effect by 50% ($ID_{50}$) was thus determined.

| Product of Example | $ID_{50}$ in mg/kg |
|---|---|
| 21 | 2.35 |

Various modifications of the products and method of the invention may be made without departing from the spirit or scope thereof and it is to be understood that the invention is intended to be limited only as defined in the appended claims.

What is claimed is:

1. A method of inhibiting angiotensin II effects in warm-blooded animals comprising administering to warm-blooded animals an angiotensin II effective inhibiting amount of at least one compound selected from the group consisting of all possible racemic isomers, enantiomers and diastereoisomers of a compound of the formula

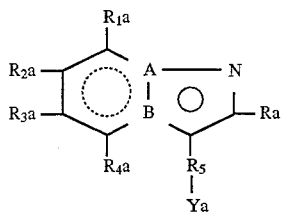

wherein one of A and B is nitrogen and the other is carbon, the dotted lines indicate that the pyridinyl ring is optionally unsaturated, Ra is alkyl of 1 to 4 carbon atoms, $R_1a$, $R_2a$, $R_3a$ and $R_4a$ are individually selected from the group consisting of hydrogen, —OH, alkoxy of 1 to 6 carbon atoms, free carboxy, carboxy esterified with alkyl of 1 to 4 carbon atoms and alkyl of 1 to 6 carbon atoms optionally substituted with at least one member of the group consisting of halogen, —OH, amino, carbamoyl and alkoxy of 1 to 4 carbon atoms, $R_5$ is C=O, Ya is —$Y_1$a—Ba—$Y_2$a wherein $Y_1$a is a phenyl, Ba is a single bond or —CONH—, $Y_2$a is a phenyl optionally substituted with at least one member of the group consisting of halogen, free, salified or esterified carboxy, —CN, tetrazolyl, pyrazolo (1–5a) pyridine, pyrazolo (1–5a) pyridine alkyl, imidazol (1–2a) pyridine and —$(CH_2)_p$—$SO_2$—Xa—$R_{14}$a, p is 0 or 1, Xa is selected from the group consisting of a single bond, —NH—and —NHCO—, $R_{14}$a is selected from the group consisting of methyl, ethyl, propyl, vinyl, allyl, pyridyl, phenyl, benzyl, pyridylmethyl, pyridylethyl, pyrimidyl, tetrazolyl, thiazolyl, diazolyl and piperidinyl, all optionally substituted with at least one member of the group consisting of halogen, —OH, alkyl and alkoxy of 1 to 6 carbon atoms, —$CF_3$, —CN and —$NO_2$.

\* \* \* \* \*